(12) United States Patent
Takahashi et al.

(10) Patent No.: US 6,607,643 B2
(45) Date of Patent: Aug. 19, 2003

(54) $NO_x$ GAS DETECTING APPARATUS

(75) Inventors: Hideaki Takahashi, Aichi-gun (JP);
Keiichi Saji, Aichi-gun (JP); Jiro Sakata, Aichi-gun (JP); Tadashi Inaba, Aichi-gun (JP); Tadashi Nakamura, Aichi-gun (JP); Yumi Masuoka, Aichi-gun (JP); Toshitaka Saito, Toyohashi (JP); Akio Tanaka, Gifu (JP)

(73) Assignees: Kabushiki Kaisha Toyota Chuo Kenkyusho, Aichi-gun (JP); Denso Corporation, Kariya (JP)

( * ) Notice: Subject to any disclaimer, the term of this patent is extended or adjusted under 35 U.S.C. 154(b) by 0 days.

(21) Appl. No.: 09/794,069

(22) Filed: Feb. 28, 2001

(65) Prior Publication Data

US 2001/0023823 A1 Sep. 27, 2001

(30) Foreign Application Priority Data

Feb. 29, 2000 (JP) .......................... 2000-053901
Oct. 3, 2000 (JP) .......................... 2000-304100

(51) Int. Cl.[7] ............................................ G01N 27/407
(52) U.S. Cl. .................. 204/425; 204/293; 204/426; 205/781
(58) Field of Search .................... 204/421–429, 204/293; 205/781

(56) References Cited

U.S. PATENT DOCUMENTS

| 4,200,511 A | * | 4/1980 | Sato et al. |
| 4,814,059 A | | 3/1989 | Nishizawa et al. |
| 4,863,583 A | * | 9/1989 | Kurachi et al. |
| 5,672,811 A | * | 9/1997 | Kato et al. |
| 6,274,016 B1 | * | 8/2001 | Hasei et al. |
| 6,319,377 B1 | * | 11/2001 | Hasei et al. |

FOREIGN PATENT DOCUMENTS

| EP | 0 880 024 A1 | 11/1998 |
| EP | 0 880 026 A1 | 11/1998 |
| EP | 0 928 965 A2 | 7/1999 |
| JP | 6-084950 | 10/1994 |
| JP | 10-318979 | 12/1998 |
| JP | 11-023521 | 1/1999 |
| JP | 11-166913 | 6/1999 |
| JP | 11-183434 | 7/1999 |

OTHER PUBLICATIONS

*Characteristics of Limiting Current–Type Oxygen Sensor*, pp 2430–2435, Keiich Saji, Journal of the Electrochemical Society vol. 134, No. 10, Oct. 1987.
*New Total–$NO_x$ Sensor based on Mixed Potential for Automobiles*, Akira Kunimoto et al., SAE Technical Paper Series 1999–01–1280, SAE International.

* cited by examiner

Primary Examiner—T. Tung
(74) Attorney, Agent, or Firm—Oblon, Spivak, McClelland, Maier & Neustadt, P.C.

(57) ABSTRACT

A $NO_x$ gas detecting apparatus including an oxygen pumping cell for removing oxygen from a measurement gas, and a $NO_x$ detecting cell positioned downstream from the oxygen pumping cell to detect concentration of $NO_x$ in the measurement gas, the $NO_x$ detecting cell being configured to measure current which flows when oxygen generated from reducing $NO_x$ is pumped, wherein the $NO_x$ detecting cell has a $NO_x$ detecting cathode made of an electrode material including at least one alloy selected from the group consisting of a Pt-Pd alloy, a Pt-Au-Pd alloy, and a Pt-Pd-Rh alloy.

8 Claims, 12 Drawing Sheets

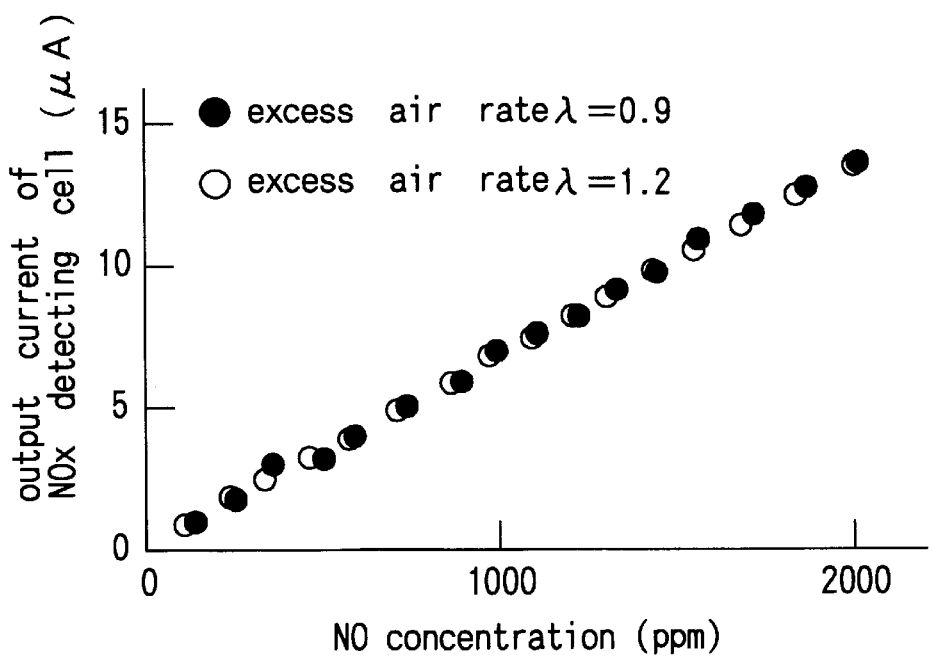
F I G. 1 1
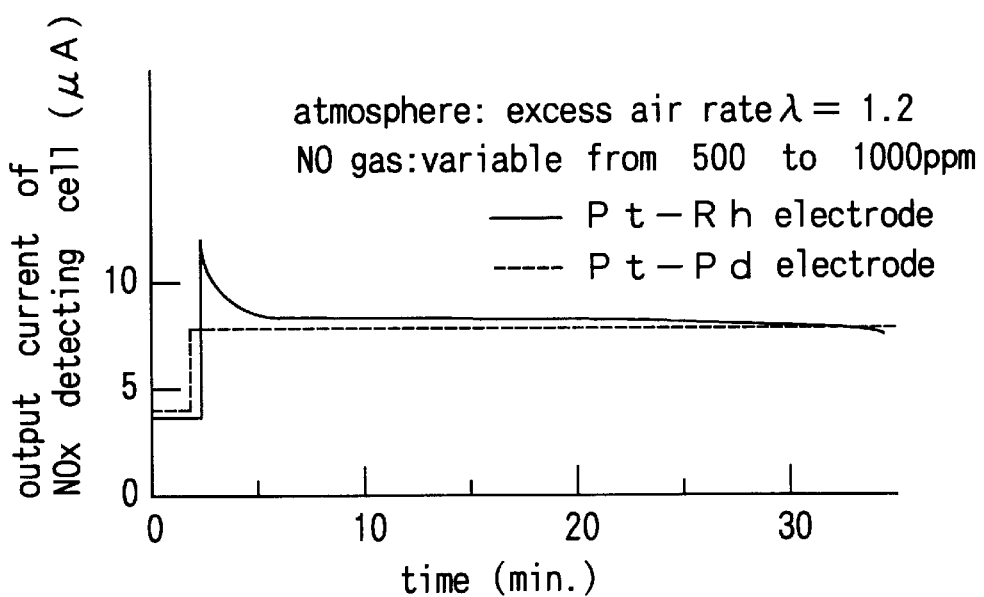
F I G. 1 2

$NO_x$ GAS DETECTING APPARATUS

BACKGROUND OF THE INVENTION

1. Field of the Invention

The present invention relates to a $NO_x$ gas detecting apparatus. More particularly, the present invention relates to a $NO_x$ gas detecting apparatus capable of detecting a nitrogen oxide gas (a $NO_x$ gas) contained in exhaust gas discharged from boilers, automobiles and the like, or in living environments with high sensitivity.

2. Description of Related Art

When voltage is applied between electrodes that are sintered onto each side of an oxygen ion conductive solid electrolyte (hereinafter referred to simply as a "solid electrolyte"), such as a stabilized zirconia as a typical example, then an oxygen pumping action is produced in that oxygen is discharged from one electrode (cathode) to the other electrode (anode).

Also, when electrodes that are sintered onto each side of a solid electrolyte (hereinafter referred to as a "cell") are exposed in an atmosphere including an oxygen bound gas, such as $NO_x$, $SO_x$, $H_2O$, $CO_2$ and the like, and when voltage is applied between the electrodes, the oxygen bound gas is decomposed around the cathode and the oxygen generated thereby is discharged to the anode by an oxygen pumping action of the solid electrolytes. Simultaneously, current follows from the anode to the cathode in proportion to the concentration of the oxygen bound gas decomposed.

The voltage at which this oxygen pumping action is initiated differs depending on each oxygen bound gas. In addition, even in the case of the same oxygen bound gas, the voltage at which an oxygen pumping action is initiated in association with gas decomposition differs depending on a material constructing the electrodes (especially the cathode) disposed onto the electrolyte. Further, when heated in an atmosphere of a low partial pressure of oxygen, an oxygen bound gas is decomposed generally into oxygen and other components which have been bounded to the oxygen. The partial pressure of oxygen of which decomposition rate reaches a certain value differs depending on each oxygen bound gas.

Taking advantage of an oxygen pumping action of a cell and difference in decomposition of an oxygen bound gas owing to a gas diffusion rate determining body, voltage applying conditions, electrode materials, or partial pressure conditions of oxygen, a gas detecting apparatus capable of detecting concentration of a specific oxygen bound gas contained in a measurement gas to be measured may be produced. Especially, a $NO_x$ gas detecting apparatus for detecting concentration of a $NO_x$ gas contained in a measurement gas has been put into actual use as a sensor for monitoring an amount of $NO_x$ gas contained in exhaust gas discharged from combustion equipment and combustion facilities such as automobiles and boilers.

It is required that a $NO_x$ detecting apparatus detect a $NO_x$ gas contained in exhaust gas in a minute amount independent of influence of oxygen which is a main component of the exhaust gas. To meet this end, a $NO_x$ detecting apparatus comprises a gas diffusion rate determining body, an oxygen pumping cell, and a $NO_x$ gas detecting cell. The gas diffusion rate determining body is constructed for restricting gas diffusion flowing into the oxygen pumping cell and the $NO_x$ detecting cell by providing a small pinhole or a porous body at an upstream stage of the oxygen pumping cell. The oxygen pumping cell is a cell for selectively removing nothing but oxygen from the measurement gas through the use of an oxygen pumping action of the solid electrolyte. Accordingly, for an cathode of the oxygen pumping cell, an electrode having a high activity relative to an oxygen gas but is inactive or low active relative to a $NO_x$ gas is used. As such an electrode, for example, a cermet electrode composed of a Pt-Au alloy and a ceramic component (hereinafter referred to as a "Pt-Au electrode") is known.

The $NO_x$ detecting cell is a cell for decomposing $NO_x$ contained in the measurement gas from which oxygen has been removed whereby a value of the current flowing between the electrodes at that time is measured. Accordingly, for a cathode of the $NO_x$ detecting cell, an electrode having a high activity relative to $NO_x$ gas is used. As such an electrode, for example, a cermet electrode composed of Pt and a ceramic component (hereinafter referred to as a "Pt electrode"), a cermet electrode composed of a Pt-Rh alloy and a ceramic component (hereinafter referred to as a "Pt-Rh electrode," and the like are known). (See, for example, Japanese Unexamined Patent Publication No. HEI 11-183434 for reference.)

A $NO_x$ gas is apt to decompose when heated in a low oxygen atmosphere containing a reduction component such as an uncombusted fuel. Consequently, in order to find out about an accurate $NO_x$ concentration in exhaust gas with the $NO_x$ gas detecting apparatus, the $NO_x$ concentration needs to be measured immediately after oxygen has been removed from the measurement gas and before the measurement gas is influenced by other components. To meet this end, in the $NO_x$ detecting apparatus, the $NO_x$ detecting cell is usually disposed at a downstream stage of the oxygen pumping cell in adjacent thereto.

The $NO_x$ gas detecting apparatus constructed as described above is produced generally by printing paste containing an electrode material on a surface of a green sheet containing a solid electrolyte, laminating it onto another integrally, and then sintering it in an atmosphere at a high temperature (in the case of a zirconia-base solid electrolyte for example at 1,400° C. or higher).

In the technical back ground described above, Pt is active for both an oxygen gas and a $NO_x$ gas, but becomes active only for oxygen by adding Au to Pt. Accordingly, a Pt-Au alloy is especially suitable as an electrode material of an oxygen pumping cell. On the other hand, Au which is contained in a Pt-Au alloy has a low temperature resistance (the melting point of 1,064° C.), and therefore heating a Pt-Au alloy at a high temperature causes Au contained in the alloy to scatter in all directions.

Due to the above reasons, there is a problem in the case of using a Pt-Au electrode as the cathode of the oxygen pumping cell, and a Pt electrode as the cathode of the $NO_x$ detecting cell. When a green sheet constructing the oxygen pumping cell and a green sheet constructing the $NO_x$ detecting cell are laminated and sintered at a high temperature, Au contained in the cathode of the oxygen pumping cell scatters and adheres to the Pt electrode of the $NO_x$ detecting cell. This causes the $NO_x$-reducing ability of the Pt electrode to be reduced.

Further, fuel used for automobiles or combustion facilities such as a boiler contains various impurities. Also, in exhaust gas discharged from combustion facilities, there exist components derived from additives contained in engine oil. These components also cause a problem of reducing electrode activity drastically if they adhere to the Pt electrode used in the $NO_x$ detecting cell no matter how minute the amount is.

Alternatively, a Pt-Rh electrode that contains a large amount of Rh relative to Pt (about 40 wt %) may be used as the electrode of the $NO_x$ detecting cell, because Rh has a high $NO_x$ reducing ability.

However, since Rh is strongly bounded to oxygen, if the electrode is left in an oxidation atmosphere, oxygen is adsorbed to Rh thereby forming an oxide film on the surface thereof. This causes a problem of lowering the $NO_x$ reducing ability. Here, in order to improve the $NO_x$ reducing ability, the oxide film formed on the surface of Rh needs to be removed so that Rh is used as a metal. Yet, there is a problem in that the reduction process takes a long time.

In addition, even if the reduction process is carried out, Rh again adsorbs oxygen with a lapse of time. Consequently, when voltage is applied to the $NO_x$ detecting cell, oxygen gas that has been adsorbed within the Pt-Rh electrode is discharged gradually immediately after the activation. Consequently, the $NO_x$ detecting cell appears to output as if there existed a $NO_x$ gas although there is no $NO_x$ gas, which results in a problem in that data with repeatability are not obtained. Accordingly, it is difficult to detect a $NO_x$ gas at a low concentration.

Further, the amount of oxygen gas adsorption to Rh greatly changes depending on oxygen concentration in the atmosphere and the lapse of time, and the rate of adsorption/desorption is rather slow. Due to these reasons, even if the measurement gas supplied to the $NO_x$ gas detecting cell is controlled to be constant in its oxygen concentration by using the oxygen pumping cell, it is difficult to keep the Pt-Rh electrode always at a constant state under the conditions where oxygen concentration in the atmosphere fluctuates depending on driving state as in the case of automobiles. Hence, it is difficult to faithfully monitor the state in which abrupt changes occur in the combustion state and thus in the amount $NO_x$ gas generated.

Also, this $NO_x$ detecting apparatus is provided with a gas diffusion rate determining body at an upstream stage of the oxygen pumping cell. Therefore, when a measurement gas is supplied to the $NO_x$ detecting cell and voltage applied between the electrodes is increased, a limiting current characteristic is exhibited, that is, the output current remains generally constant irrespective of applied voltage. The minimum voltage at which the output voltage becomes constant (hereinafter referred to as a "limiting current generating voltage") differs depending on the types of oxygen bound gas. For example, exhaust gas contains $H_2O$ and $CO_2$ other than $NO_x$ gas, and $H_2O$ and $CO_2$ are less decomposable than $NO_x$ so that its limiting current generating voltage is higher than that of $NO_x$.

Also, the limiting current generating voltage relative to oxygen bound gas differs depending on the composition of the electrodes. In the case of detecting concentration of $NO_x$ in the exhaust gas using the $NO_x$ detecting cell, the cathode of the $NO_x$ detecting cell having a high limiting current generating voltage relative to $NO_x$ makes it difficult to detect $NO_x$ at a low concentration with high accuracy. This is because $H_2O$ and $CO_2$ are decomposed along with $NO_x$ thereby to produce oxygen.

SUMMARY OF THE INVENTION

The present invention has been made in view of the above circumstances and has an object to overcome the above problems and to provide a $NO_x$ gas detecting apparatus capable of detecting a $NO_x$ gas accurately and stably over a long period of time independent of adherents to the cathode of the $NO_x$ detecting cell, such as Au, impurities contained in exhaust gas, and the like.

Another object of the present invention is to provide a $NO_x$ gas detecting apparatus which is excellent in startability, and which is capable of faithfully detecting abrupt fluctuations in the $NO_x$ concentration.

Yet, another object of the present invention is to provide a $NO_x$ gas detecting apparatus capable of accurately detecting $NO_x$ at a low concentration even if the measurement gas contains other oxygen bound gases such as $H_2O$, $CO_2$ and the like besides $NO_x$.

To achieve the objects and in accordance with the purpose of the present invention, as embodied and broadly described herein, in the present invention, a $NO_x$ gas detecting apparatus comprises an oxygen pumping cell for removing oxygen from a measurement gas, a $NO_x$ detecting cell for measuring $NO_x$ contained in the measurement gas from which oxygen has been removed. The $NO_x$ detecting cell comprises, as the cathode, an electrode composed of at least one selected from the group consisting of: a Pt-Pd alloy; a Pt-Au-Pd alloy; and a Pt-Pd-Rh alloy.

The $NO_x$ gas detecting apparatus of the present invention configured as constructed above uses an alloy including Pd as the cathode of the $NO_x$ detecting cell so that the activity relative to $NO_x$ is enhanced drastically. In addition, the $NO_x$ gas detecting apparatus allows the activity relative to $NO_x$ not to be lowered even if Au or other impurities contained in exhaust gas adhere to the electrode. Further, the Pt-Pd alloy or the Pt-Au-Pd alloy is excellent in oxidation resistance and fast in the adsorption/desorption rate as compared with the Pt-Rh alloy. Therefore, the $NO_x$ gas detecting apparatus is capable of detecting $NO_x$ accurately and stably over a long period of time. Also, the $NO_x$ gas detecting apparatus is excellent in startability and capable of faithfully detecting abrupt fluctuations in the $NO_x$ concentration, and also excellent in responsivity and repeatability. Further, through optimization of the electrode composition, the $NO_x$ gas reducing ability may be further improved as compared with the Pt electrode or the Pt-Rh electrode, thereby allowing a $NO_x$ gas to be detected in a minute amount accurately.

In the case that the $NO_x$ gas detecting apparatus comprises, as the cathode, an electrode composed of a Pt-Pd-Rh alloy, since Rh is further added to the Pt-Pd alloy, the limiting current generating voltage relative to a $NO_x$ gas is lowered, and thus a $NO_x$ gas may be discharged at a low voltage. As the result, even if the measurement gas contains oxygen bound gases (for example $H_2O$) other than $NO_x$, little influence is exerted on output current generated when $NO_x$ is discharged, and therefore $NO_x$ is detected at a low concentration with higher accuracy.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 11 is a view showing the relation between a NO gas concentration and an output current of a $NO_x$ gas detecting apparatus having a Pt-Pd electrode as a cathode of a $NO_x$ detecting cell;

FIG. 12 is a view showing responsivity of a $NO_x$ gas detecting apparatus having a Pt-Pd electrode or a Pt-Rh electrode as a cathode of a $NO_x$ detecting cell;

DETAILED DESCRIPTION OF THE PREFERRED EMBODIMENTS

Figure 1:
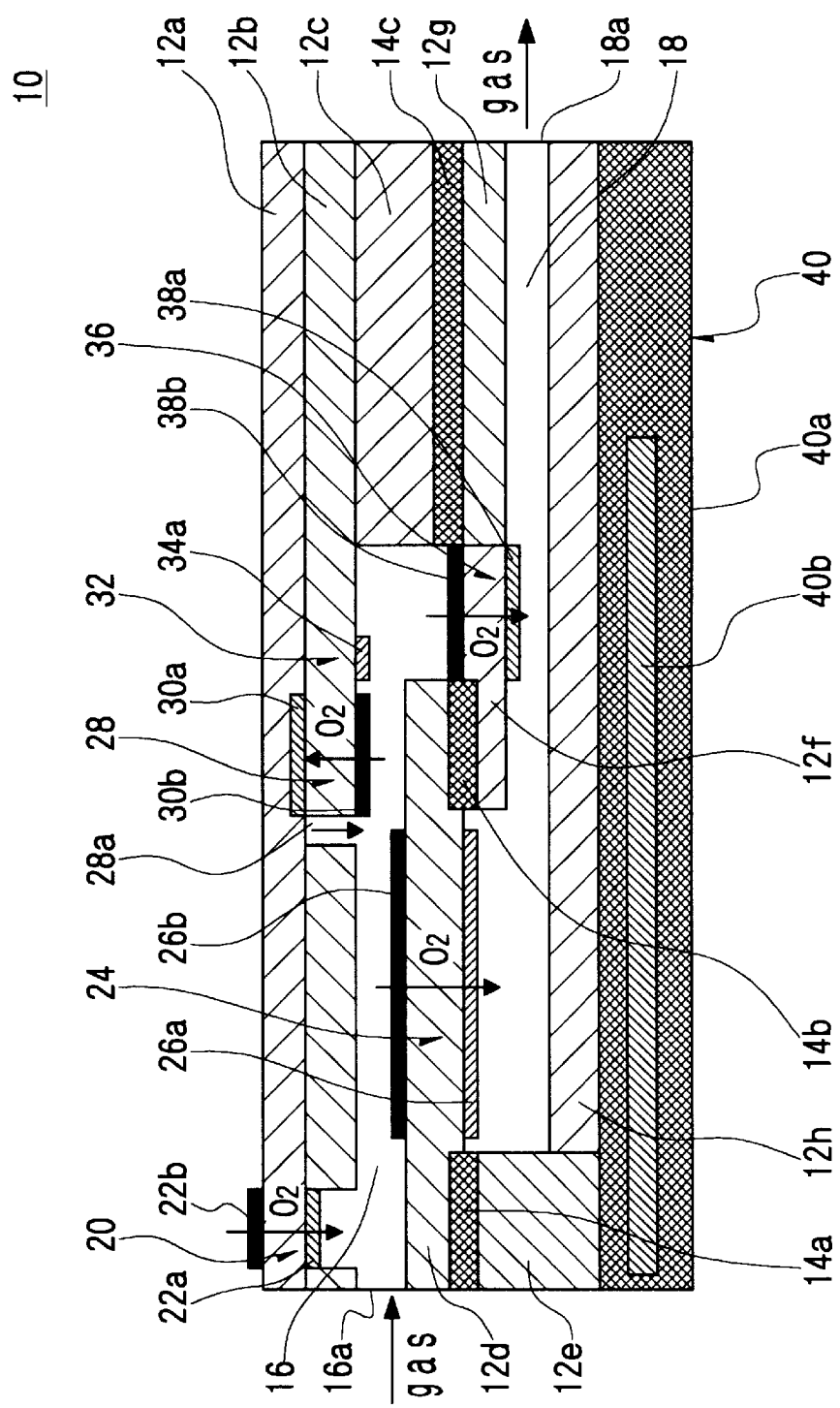
FIG. 1 is a cross sectional view showing a $NO_x$ detecting apparatus consistent with the present invention.

A detailed description of preferred embodiments of the present invention will now be given referring to the accompanying drawings. In FIG. 1, there is shown a cross section of a $NO_x$ gas detecting apparatus (hereinafter referred to as a "detecting apparatus") consistent with a first preferred embodiment of the present invention. In FIG. 1, the detecting apparatus 10 is constructed of solid electrolytes 12a–12h, insulating layers 14a, 14b, 14c, each of which are disposed between the solid electrolytes 12d and 12e, between the solid electrolytes 12d and 12f, and between the solid electrolytes 12c and 12g, respectively, and an insulating layer 40a disposed at the undermost layer.

Disposed inside the detecting apparatus 10 is a gas introducing chamber 16 and a gas discharging chamber 18. The gas introducing chamber 16 is a closed space provided with a gas introducing section 16a from which a measurement gas is introduced thereinto by gas diffusion. Inner walls of the gas introducing chamber 16 is constructed of the solid electrolytes 12b, 12c, 12f and 12d. Also, the gas discharging chamber 18 is a closed space provided with a gas discharging section 18a for discharging an oxygen gas which has been discharged thereinto through the solid electrolytes 12d and 12f. Inner walls of the gas discharging chamber 18 is constructed of the solid electrolytes 12d, 12e, 12f, 12g and 12h.

In addition, the detecting apparatus 10 comprises an oxygen gas supplying cell 20, an oxygen pumping cell 24, an oxygen reference electrode generating cell 28, an oxygen monitoring cell 32, a $NO_x$ detecting cell 36, and a heater section 40.

The oxygen gas supplying cell 20 comprises the solid electrolyte 12a as well as an anode 22a and a cathode 22b disposed on each side thereof. The anode 22a and the cathode 22b are connected to a power source (not illustrated) for applying a predetermined voltage. The oxygen gas supplying cell 20 is a cell for supplying oxygen to the measurement gas introduced into the gas introducing chamber 16, and is disposed in the vicinity of the gas introducing section 16a. The anode 22a and the cathode 22b are disposed on the inner wall of the gas introducing chamber 16 and the outer wall of the detecting apparatus 10, respectively.

The oxygen pumping cell 24 comprises the solid electrolyte 12d as well as an anode 26a and a cathode 26b disposed on each side thereof. The anode 26a and the cathode 26b are connected to a power source (not illustrated) for applying a predetermined voltage. The oxygen pumping cell 24 is a cell for selectively discharging, to the gas discharging chamber 18, nothing but oxygen that exists in the measurement gas which has been introduced into the gas introducing chamber 16. The oxygen pumping cell 24 is disposed at a downstream stage of the oxygen supplying cell 20. The anode 26a and the cathode 26b are disposed on the inner wall of the gas discharging chamber 18 and the inner wall of the gas introducing chamber 16, respectively.

The oxygen reference electrode generating cell 28 comprises the solid electrolyte 12b as well as an anode 30a and a cathode 30b disposed on each side thereof. The anode 30a and the cathode 30b are connected to a power source (not illustrated) for applying a predetermined voltage. The oxygen reference electrode generating cell 28 is a cell for forming a reference electrode that will be necessary upon measuring an amount of residual oxygen remaining in the measurement gas after the oxygen pumping cell 24 has removed oxygen therefrom. The oxygen reference electrode generating cell 28 is disposed at a downstream stage of the oxygen pumping cell 24. The anode 30a is disposed at the interface between the solid electrolytes 12a and 12b, and the cathode 30b is disposed on the inner wall of the gas introducing chamber 16. Further, the solid electrolyte 12b is provided with an oxygen discharging exit 28a adjacent to the oxygen reference electrode generating cell 28 so that the oxygen collected around the anode 30a flows back into the gas introducing chamber 16.

The oxygen monitoring cell 32 comprises the solid electrolyte 12b, the electrode 34a disposed on the inner wall of the gas introducing chamber 16, and the anode 30a. In other words, the oxygen monitoring cell 32 is constructed to share the anode 30a with the oxygen reference electrode generating cell 28. The electrode 34a and the anode 30a are connected to a voltmeter (not illustrated) for measuring potential difference which occurs between the two electrodes. The oxygen monitoring cell 32 is a cell for measuring an amount of residual oxygen remaining in the measurement gas with the anode 30a of the oxygen reference electrode generating cell 28 as the reference electrode, and is disposed in adjacent to the oxygen reference electrode generating cell 28.

The $NO_x$ detecting cell 36 comprises the solid electrolyte 12f as well as an anode 38a and a cathode 38b disposed on each side thereof. The anode 38a and the cathode 38b are connected to a power source (not illustrated) for applying a predetermined voltage, and to an ammeter (not illustrated) for measuring current flows between the two electrodes. The $NO_x$ detecting cell 36 is a cell for decomposing a $NO_x$ gas contained in the measurement gas to measure an amount of oxygen generated at that time, and is disposed at a downstream stage of the oxygen pumping cell 24 adjacent thereto. The anode 38a is disposed on the inner wall of the gas discharging chamber 18, while the cathode 38b is disposed on the inner wall of the gas introducing chamber 16.

The heater section 40 is constructed of a heater 40b made from a metal and a ceramic component and disposed within an insulation layer 40a. The heater section 40 is used to heat the solid electrolytes 12a, 12b, 12d and 12f until they exhibit an oxygen pumping action, or to keep the detecting apparatus 10 at a predetermined temperature. In the example shown in FIG. 1, the heater section 40 is disposed at a lower edge of the detecting apparatus 10.

Here, a material for forming the solid electrolytes 12a–12h does not have to be limited to any specific one as long as it exhibits oxygen ion conductivity. Zirconia-base solid electrolytes ($ZrO_2$–$M_2O_3$ solid solution or $ZrO_2$–MO solid solution, provided M=Y, Yb, Gd, Mg or the like), ceria-base solid electrolytes ($CeO_2$–$M_2O_3$ solid solution or $CeO_2$–MO solid solution, provided M=Y, Sm or the like), and bismuth oxide-base solid electrolytes ($Bi_2O_3$–$WO_3$ solid solution or the like) are some suitable examples.

Especially, zirconia-base solid electrolytes are suitable as a material for the solid electrolytes 12a–12h in view of the stability in exhaust gas. Also, $ZrO_2$ with addition of $Y_2O_3$ in an amount of 5 to 8 mol % has excellent thermal impact resistance and high oxygen ion conductivity so that it is especially suitable as a material for the solid electrolytes 12a–12h.

The insulating layers 14a, 14b and 14c are used to electrically separate the oxygen pumping cell 24 and the $NO_x$ detecting cell 36. Accordingly, a suitable material for the insulating layers 14a, 14b and 14c has high insulation resistance at the temperature at which the solid electrolytes 12a–12h exhibit the oxygen pumping action. Alumina, spinel, mullite, cordierite, and the like are some suitable examples.

Further, regarding the electrodes used in the $NO_x$ detecting cell 36, at least the cathode 38b needs to be a cermet electrode composed of a Pt-Pd alloy or a Pt-Au-Pd alloy with a ceramic component (hereinafter, the former is referred to as a "Pt-Pd electrode" and the latter is referred to as a "Pt-Au-Pd electrode").

When a Pt-Pd alloy or a Pt-Au-Pd alloy is used to construct part of the cathode 38b, it is preferred that an amount of Pd added to Pt (=100×Pd/(Pt+Pd)) is 1 wt % or more. If Pd is added to Pt in an amount less than 1 wt %, the cathode 38b becomes less active relative to $NO_x$, which is not desirable. In addition, in order to obtain the cathode 38b which has activity equally high, or higher than a conventionally used Pt electrode or Pt-Rh electrode, it is preferred that an amount of Pd added to Pt be 90 wt % or less. More preferably, Pd is added in an amount of 5 to 40 wt %.

Also, when a Pt-Au-Pd alloy is used to construct the cathode 38b, by making a weight ratio of Pd to Au (hereinafter referred to as a "Pd/Au ratio") 1.67 or more, the thus obtained electrode becomes more active relative to $NO_x$ as compared with the Pt-Au electrode which does not contain Pd. By making the Pd/Au ratio 6.67 or more, an electrode of which activity relative to $NO_x$ is generally equal to that of the Pt electrode or the Pt-Rh electrode is obtained. Further, if the addition amount of Pd and the addition amount of Au in the Pt-Au-Pd alloy are set within the diagonally shaded area shown in FIG. 10, an electrode of which activity relative to $NO_x$ is equally high, or higher than the Pt electrode or Pt-Rh electrode is obtained.

The ceramic component constructing other part of the cathode 38b is added in order to enhance adherence between the cathode 38b and the solid electrolyte 12f. Accordingly, the composition and the addition amount may be decided arbitrarily as long as good adherence is obtained between them. Here, if the addition amount of ceramic is too large, the conductivity of the cathode 38b is undesirably lowered. Normally, a ceramic component having the same composition with the solid electrolyte 12f is added to the cathode 38b in a degree of 10 to 20 wt %.

Here, a material forming the other electrodes does not have to be limited to any specific one as long as it exhibits high activity relative to an oxygen gas and an oxygen bound gas. Yet, in order to suppress the decomposition of $NO_x$ gas, the cathode 26b of the oxygen pumping cell 24 needs to be composed of a material having high activity relative to an oxygen gas but no or low activity relative to a $NO_x$ gas. A Pt-Au electrode is one suitable example. Due to the same reasons, it is required that electrodes exhibiting high activity only relative to an oxygen gas be used as the anode 30a and the cathode 30b of the oxygen reference electrode generating cell 28, and also as the electrode 34a of the oxygen monitoring cell 32.

The insulating layer 40a of the heater section 40 is constructed of a material having high insulation resistance at a temperature at which the solid electrolytes 12a–12h exhibit an oxygen pumping action. Alumina, spinel, mullite, cordierite, and the like are some suitable examples. The heater 40b is normally composed of metal with excellent oxidation resistance (for example, Pt and the like) and a ceramic component.

Next, description is given to a general scheme to detect a $NO_x$ gas contained in exhaust gas using the detecting apparatus 10 shown in FIG. 1. First, the whole body of the detecting apparatus 10 is placed in exhaust gas. Then, the detecting apparatus 10 is heated using the heater section 40 such that it is maintained at a temperature at which the solid electrolytes 12a–12h exhibit an oxygen pumping action (for example 700° C.). In this case, the measurement gas diffuses and flows into the gas introducing chamber 16 through the gas introducing section 16a.

Under this condition, a predetermined voltage (for example, from 0.3 to 0.6 V) is applied between the anode 22a and the cathode 22b of the oxygen gas supplying cell 20. Here, in the case of exhaust gas in a lean atmosphere (an excess oxygen atmosphere), oxygen contained in the exhaust gas outside the detecting apparatus 10 is supplied to the gas introducing chamber 16 through an oxygen pumping action of the solid electrolyte 12a. On the contrary, in the case of exhaust gas in a rich atmosphere (an excess fuel atmosphere), the exhaust gas contains little oxygen but usually contains $H_2O$ gas of 5 to 10%. Consequently, this $H_2O$ gas is decomposed around the cathode 22b and the oxygen generated through the decomposition is supplied to the gas introducing chamber 16 by oxygen pumping action.

A $NO_x$ gas has a characteristic that it is apt to decompose into a nitrogen gas and an oxygen gas when heated at a high temperature under a low oxygen atmosphere. Accordingly, in order to accurately detect a $NO_x$ gas contained in the measurement gas at a low concentration, decomposition of the $NO_x$ gas needs to be suppressed until the measurement gas reaches the $NO_x$ detecting cell 36. In the detecting apparatus 10 consistent with this preferred embodiment, the oxygen gas supplying cell 20 supplies oxygen into the gas introducing chamber 16. Therefore, even if the atmosphere of the exhaust gas changes to lean or to rich, inside the gas introducing chamber 16 is controlled to be a lean atmosphere at all times, thereby suppressing decomposition of $NO_x$ gas.

Thereafter, a mixture gas of the measurement gas flowing through the gas introducing section 16a and the oxygen gas supplied from the oxygen gas supplying cell 20 diffuses and reaches the oxygen pumping cell 24. The cathode 26b of the oxygen pumping cell 24 is formed of a material that exhibits high oxygen reducing ability but no $NO_x$ reducing ability at a predetermined voltage (for example, 0.3 V) or less. Consequently, when an adequate voltage is applied between the anode 26a and the cathode 26b, nothing but an oxygen gas contained in the measurement gas is selectivity discharged to the gas discharging chamber 18 by an oxygen pumping action.

In addition, the discharge state of oxygen at this time is monitored by the oxygen reference electrode generating cell 28 and the oxygen gas monitoring cell 32. That is, when a predetermined voltage (for example, 0.5 V) is applied between the anode 30a and the cathode 30b of the oxygen reference electrode generating cell 28, oxygen gas contained in the measurement gas which exists in the gas introducing chamber 16 is collected to the side of anode 30a by the oxygen pumping action. Since the anode 30a is disposed at the interface between the solid electrolytes 12a and 12b, the side of anode 30a is assumed to be in an oxygen atmosphere of almost 100%. Consequently, by measuring a potential difference generated between the anode 30a and the electrode 34a of the oxygen monitoring cell 32 with the anode 30a as the reference electrode, it is possible to measure the partial pressure of oxygen in the measurement gas that has passed through the oxygen pumping cell 24.

In the actual measurement of a $NO_x$ gas concentration, it is preferred that an applied voltage to the oxygen pumping cell 24 be controlled such that an electromotive force of the oxygen monitoring cell 32 is made constant (for example, 0.3 V). This makes it possible to supply the measurement gas to be supplied to the $NO_x$ detecting cell 36 such that the measuring gas contains no oxygen gas or oxygen gas at a certain concentration.

Then, the oxygen gas which has been controlled its oxygen concentration diffuses and reaches the $NO_x$ detecting cell 36. Here, when a predetermined voltage (for example, 0.5 V) is applied to the anode 38a and the cathode 38b of the $NO_x$ detecting cell 36, the $NO_x$ gas first adheres to the cathode 38b, and then decomposes at the interface between the cathode 38b and the solid electrolyte 12f. Oxygen generated by the $NO_x$ gas decomposition is discharged to the gas discharging chamber 18 by an oxygen pumping action of the solid electrolyte 12f. At this time, current flows between the anode 38a and the cathode 38b in proportion to the concentration of the $NO_x$ gas. Hence, by measuring the value of the current with a not illustrated ammeter, the $NO_x$ gas concentration is measured as well.

Here, in the case where an oxygen gas contained in the measurement gas has been completely removed by the oxygen pumping cell 24, the $NO_x$ gas concentration may be known directly from the value of the current flowing through the $NO_x$ detecting cell 36. On the other hand, in the case where the measurement gas supplied to the $NO_x$ detecting cell 36 has been controlled to have a certain oxygen concentration value, the current value flowing through the $NO_x$ detecting cell 36 is corrected using a value of residual oxygen concentration detected by the oxygen monitoring cell 32, whereby the $NO_x$ gas concentration contained in the measurement gas is detected with high accuracy.

Figure 2:
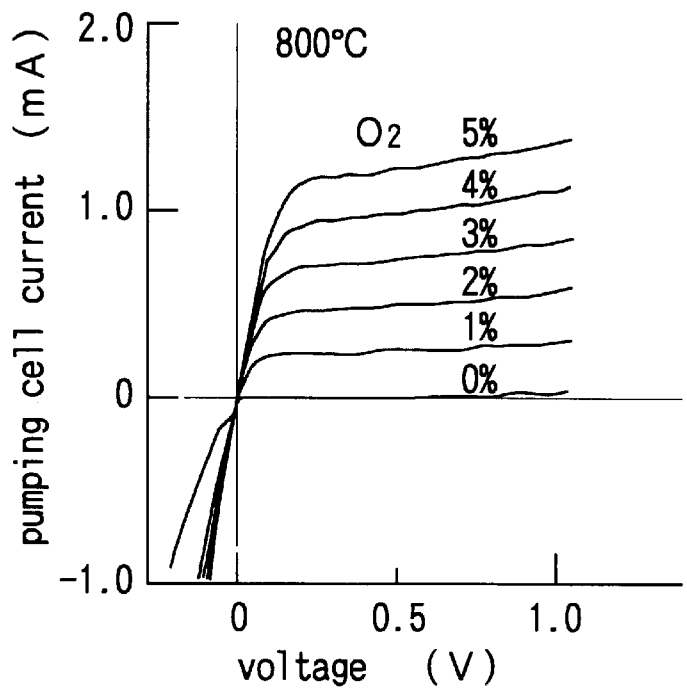
FIG. 2 is a view showing current-voltage characteristics with respect to an oxygen gas exhibited by oxygen pumping cells each having a Pt-Au electrode as a cathode.

Next, description is given to operations of the detecting apparatus 10 consistent with this preferred embodiment of the present invention. As the cathode 26b of the oxygen pumping cell 24, generally, a Pt-Au electrode which is active relative to oxygen and inactive relative to $NO_x$ is used. FIG. 2 shows current-voltage characteristics with respect to an oxygen gas exhibited by the oxygen pumping cell 24 having a Pt-Au electrode as the cathode 26b. FIG. 2 shows the results obtained when the oxygen pumping cell 24 was heated to 800° C. and measurement gases with different oxygen concentrations were supplied. From FIG. 2, it is apparent that the Pt-Au electrode exhibited the limiting current characteristic with respect to oxygen: That is, the output current increased in proportion to the voltage and then became saturated. It is also apparent that a high output current was obtained at a relatively low voltage. These findings show that the Pt-Au electrode has high activity relative to oxygen.

Figure 3:
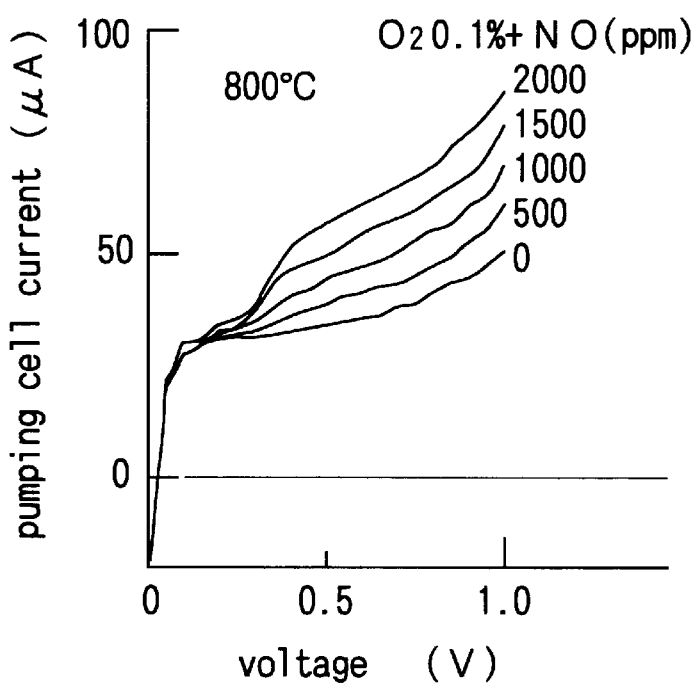
FIG. 3 is a view showing current-voltage characteristics with respect to an oxygen gas+a NO gas exhibited by an oxygen pumping cell having a Pt-Au electrode as a cathode.

Further, FIG. 3 shows current-voltage characteristics with respect to a NO gas exhibited by the oxygen pumping cell 24 having a Pt-Au electrode as the cathode 26b. FIG. 3 also shows the results obtained when the oxygen pumping cell 24 was heated to 800° C. and the measurement gases containing oxygen of 0.1% and NO gases of different concentrations were supplied. From FIG. 3, it is apparent that the Pt-Au electrode exhibited the limiting current characteristic with respect to the $NO_x$ concentration: That is, when the voltage exceeded 0.3 V, the output current became saturated. It is also apparent that the output current gradually increased as the voltage increased. These findings show that the Pt-Au electrode has low activity relative to a $NO_x$ gas.

Figure 4:
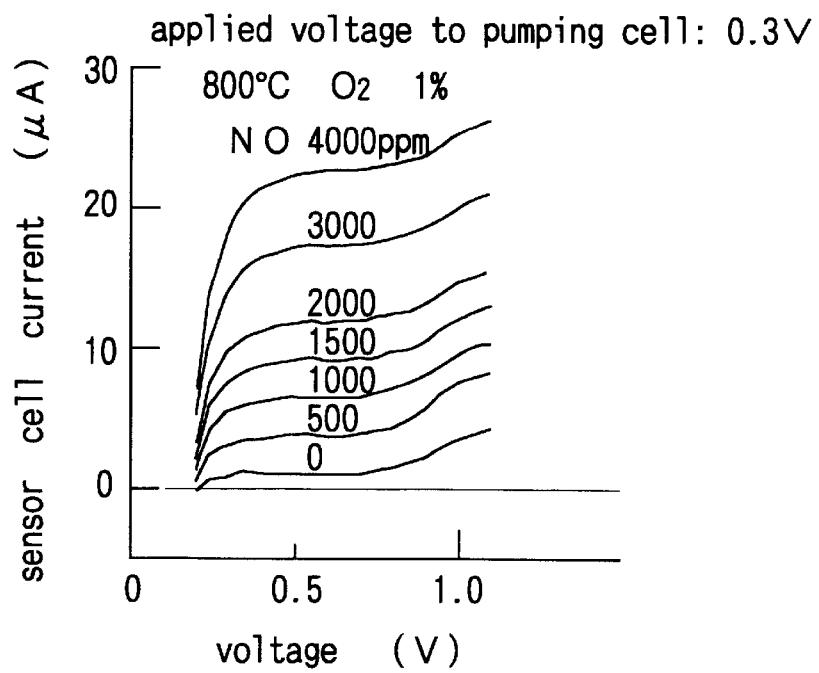
FIG. 4 is a view showing current-voltage characteristics with respect to a NO gas exhibited by $NO_x$ detecting a cell having a Pt electrode or a Pt-Rh electrode as a cathode.

Unlike a Pt-Au electrode, on the other hand, a Pt electrode or a Pt-Rh electrode is known to have high activity relative to a $NO_x$ gas. FIG. 4 shows current-voltage characteristics with respect to a NO gas exhibited by the $NO_x$ detecting cell 36 having a Pt electrode or a Pt-Rh electrode as the cathode 38b. FIG. 4 shows the results obtained when the detecting apparatus 10 comprising the $NO_x$ detecting cell 36 was heated to 800° C. and measurement gases containing oxygen of 1% and NO gasses of various concentrations were supplied to the detecting apparatus 10 while applying a voltage of 0.3 V to the oxygen pumping cell 24. From FIG. 4, it is apparent that the Pt electrode or the Pt-Rh electrode exhibited the limiting current characteristic with respect to a $NO_x$ gas when the voltage exceeded about 0.3 V. That is, the output current increased in proportion to the voltage and became saturated. It is also apparent that a high output current was obtained at a relatively low voltage.

Accordingly, the Pt electrode or the Pt-Rh electrode naturally has high $NO_x$ reducing ability as shown in FIG. 4. However, if Au adheres thereto, the $NO_x$ reducing ability lowers drastically and characteristics as shown in FIG. 3 is exhibited. As the result, it becomes difficult to detect a $NO_x$ at a low concentration with high accuracy.

The same phenomena occurs in the case when impurities in exhaust gas adhere to the Pt electrode or the Pt-Rh electrode. Such decrease in the reducing ability is considered to occur due to the following reason. That is, Au or impurities in exhaust gas adhere to the surface of Pt, whereby $NO_x$ adsorption/desorption ability of the Pt surface lowers, and thus the $NO_x$ reducing ability is lowered.

On the contrary, if a Pt-Pd electrode or a Pt-Au-Pd electrode is used as the cathode 38b of the $NO_x$ detecting cell 36, it is possible to drastically restrict lowering of the $NO_x$ gas reducing ability due to adherents to the Pt surface, such as Au, impurities in exhaust gas, and the like. Also, depending on the alloy component, it is possible to obtain an electrode with higher $NO_x$ reducing ability than that of Pt electrode. This is considered that because Pd having a higher $NO_x$ adsorption ability is added to Pt, the electrode adsorbs $NO_x$ gas more easily.

Further, the Pt-Pd alloy or the Pt-Au-Pd alloy is less oxdizable and fast in the oxygen gas adsorption/desorption as compared with the Pt-Rh alloy. Therefore, it does not occur that an oxygen gas is discharged from inside the electrode gradually right after activation. Accordingly, the detecting apparatus 10 comprising a Pt-Pd electrode or a Pt-Au-Pd electrode as the cathode 38b of the $NO_x$ detecting cell 36 is excellent in the startability and capable of detecting a $NO_x$ gas at a low concentration with high accuracy. In addition, this detecting apparatus 10 is capable of faithfully monitoring even in the condition where abrupt change occurs in the combustion state or the $NO_x$ concentration.

Hereinafter, description is given to a detecting apparatus consistent with a second preferred embodiment of the present invention. The detecting apparatus consistent with this preferred embodiment comprises, as a cathode of a $NO_x$ detecting cell, a cermet electrode composed of a Pt-Pd-Rh alloy and a ceramic component (hereinafter referred to as a "Pt-Pd-Rh electrode").

Here, when a Pt-Pd-Rh alloy is used to construct part of the cathode, it is preferred that an amount of Pd added to Pt (=100×Pd/(Pt+Pd)) be 1 wt % or more. If the addition amount of Pd is less than 1 wt %, the cathode becomes less active relative to $NO_x$, which is undesirable. In addition, in order to obtain the cathode having activity equally high, or higher than a conventionally used Pt electrode or Pt-Rh electrode, it is preferred that an amount of Pd added to Pt be 90 wt % or less. More preferably, Pd is added in an amount of 5 to 40 wt %.

Also, when the Pt-Pd-Rh alloy is used, it is preferred that an addition amount of Rh (=100×Rh/(Pt+Pd+Rh)) be 30 wt % or less. If an addition amount of Rh exceeds 30 wt %, the electrode resistivity and the cell resistivity increase, and thus the limiting current generating voltage becomes high, which is nor desirable. In addition, an amount of oxygen gas adheres to the electrode increases, thereby undesirably causing the startability of the detecting cell to be decreased.

Also, the Pt-Pd-Rh electrode may be used as it is sintered to the solid electrolytes, Yet, it is preferred that heat treatment be conducted as follows after sintering the electrodes. That is, the electrodes are heated at a predetermined temperature for a predetermined period of time in an atmosphere while applying a predetermined voltage between the electrodes. The heat treatment as above achieves an effect of lowering the limiting current generating voltage of the Pt-Pd-Rh electrode relative to $NO_x$ gas. The most suitable heat treatment condition differs depending on the electrode component, yet, for example, the following condition achieves a sufficient effect: the heat treatment temperature of 900° C., the applied voltage of 1 V, and the heating time of about 10 minutes.

The ceramic component constructing other part of the cathode is added in order to enhance adherence between the cathode and the solid electrolyte. Accordingly, the composition and the addition amount may be decided arbitrary as long as good adherence is obtained between them. Normally, a ceramic component having the same composition with the solid electrolyte onto which the cathode is sintered is added to in a degree of 10 to 20 wt %. In these two points, the detecting apparatus of this embodiment is the same as the detecting apparatus 10 of the first preferred embodiment. In addition, the detecting apparatus has the same configuration as the detecting apparatus 10 of the first preferred embodiment other than the cathode of the detecting cell, so description thereof is omitted.

Next, description is given to operation of the detecting apparatus of this preferred embodiment. The adsorption/desorption of an oxygen bound gas, the dissociation of oxygen, and the ability to ionize oxygen differ depending on the electrode material. That is, Pt is a metal, which is weak in the $NO_x$ adsorption, but strong in the dissociation of oxygen from the $NO_x$ gas and the ability to ionize oxygen. Pd is a metal, which is strong in the $NO_x$ adsorption ability, but weak in the dissociation of the $NO_x$ gas, and also low in the ability to ionize oxygen. On the other hand, Rh is a metal which is the strongest in the $NO_x$ adsorption among noble metals, and the dissociation of the $NO_x$ gas and the ability to ionize oxygen is low.

Accordingly, an electrode composed solely of Pt is weak in the $NO_x$ adsorption so that adherents have great influence. Yet, if Pd which has strong $NO_x$ adsorption is added to Pt, influence of adherents is reduced. In addition, the $NO_x$ which adheres to the electrode is dissociated into nitrogen and oxygen, and the oxygen dissociated therefrom is ionized. As the result, a Pt-Pd electrode has high $NO_x$ reducing ability than that of a Pt electrode.

However, the limiting current generating voltage relative to an oxygen bound gas differs depending on the electrode component and the type of the oxygen bound gas. For example, in the case of the Pt-Pd electrode described above, the limiting current generating voltage relative to a $NO_x$ gas is about 0.3 V, which is relatively high. The exhaust gas contains oxygen bound gases, other than $NO_x$, such as $H_2O$, $CO_2$ and the like in a large amount. Generally, the limiting current generating voltage with respect to $H_2O$ or $CO_2$ is higher than that of $NO_x$. Accordingly, in the case where the limiting current generating voltage of the electrode with respect to $NO_x$ is high, not only $NO_x$ but also $H_2O$, $CO_2$ and the like are discomposed simultaneously thereby to produce oxygen. When detecting a $NO_x$ gas at a low concentration contained in exhaust gas, the thus produced oxygen will be an measurement error factor, which is not negligible.

On the contrary, Rh adsorbs a $NO_x$ gas and more strongly. Hence, adding Rh to the Pd electrode even in a small amount, the $NO_x$ reducing ability is sufficiently enhanced. As the result, the limiting current generating voltage of the Pt-Pd-Rh electrode relative to a $NO_x$ gas becomes lower than that of the Pt-Pd electrode. Therefore, influence exerted by decomposition of $H_2O$ and $CO_2$ on the output current is reduced so that $NO_x$ is measured accurately at a low concentration.

Thereafter, heat treatment may be conducted as follows. That is, after the Pt-Pd-Rh electrode has been sintered to the surface of the solid electrolyte, it is heated in an atmosphere while applying voltage. By conducting the heat treatment, the limiting current generating voltage relative to a $NO_x$ gas further shifts toward a lower voltage. It is considered that by heating the electrode while applying a voltage, a thin oxide film is formed on the surface of the Pt-Pd-Rh electrode, and this oxide film controls the diffusion rate of oxygen.

WORKING EXAMPLE 1

A sample of electrode paste was made by adding Au and other noble metal powder to Pt in order to seek for a electrode material of which $NO_x$ gas reducing ability does not decrease even when Au is adhered to Pt.

First, $ZrO_2$ green sheets were made in the following procedures. That is, METOLOSE (manufactured by Shin-Etsu Chemical Co., Ltd.) was added to 8Y-$ZrO_2$ powder (manufactured by TOSOH Corporation) as binder in an amount of 4 wt %, and then stirred and mixed. Next, glycerine of 1.5 wt % and water of 2.1 wt % were added and further mixed. The thus obtained ceramic paste was subjected to a kneading process repeatedly for 5 to 6 times. Then, the ceramic paste was molded by extrusion molding using a molding machine with dies attached thereto, whereby $ZrO_2$ green sheets each having a 1.0 mm thickness were obtained.

Figure 5:
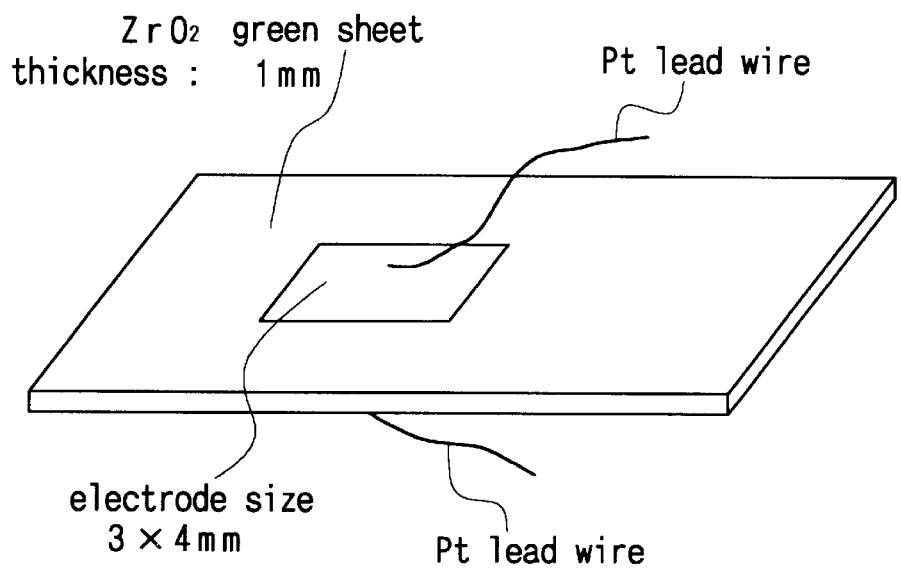
FIG. 5 is an oblique view showing an electrode examining cell.

Next, electrode paste having predetermined composition was printed on the front surface (a measurement electrode) and the rear surface (a reference electrode) of the $ZrO_2$ green sheets by screen printing. Then, they were sintered in an atmosphere under the condition of 1,430° C. for one hour to make cells for examining electrodes. The electrode examining cells had a shape as shown in FIG. 5, and the area of the electrode was 3×4 mm. Further, the component of the electrode paste used for constructing the measurement electrode and the reference electrode is shown in Table 1.

TABLE 1

| Sample No. | Measurement Electrode | Reference Electrode |
|---|---|---|
| 1 | Pt-10 wt % $ZrO_2$ | Pt-10 wt % $ZrO_2$ |
| 2 | Pt-10 wt % $ZrO_2$-3 wt % Au | Pt-10 wt % $ZrO_2$ |
| 3 | Pt-10 wt % $ZrO_2$-3 wt % Au-10 wt % Ru | Pt-10 wt % $ZrO_2$ |
| 4 | Pt-10 wt % $ZrO_2$-3 wt % Au-10 wt % Ir | Pt-10 wt % $ZrO_2$ |
| 5 | Pt-10 wt % $ZrO_2$-3 wt % Au-10 wt % Pd | Pt-10 wt % $ZrO_2$ |
| 6 | Pt-10 wt % $ZrO_2$-3 wt % Au-10 wt % Rh | Pt-10 wt % $ZrO_2$ |

Figure 6:
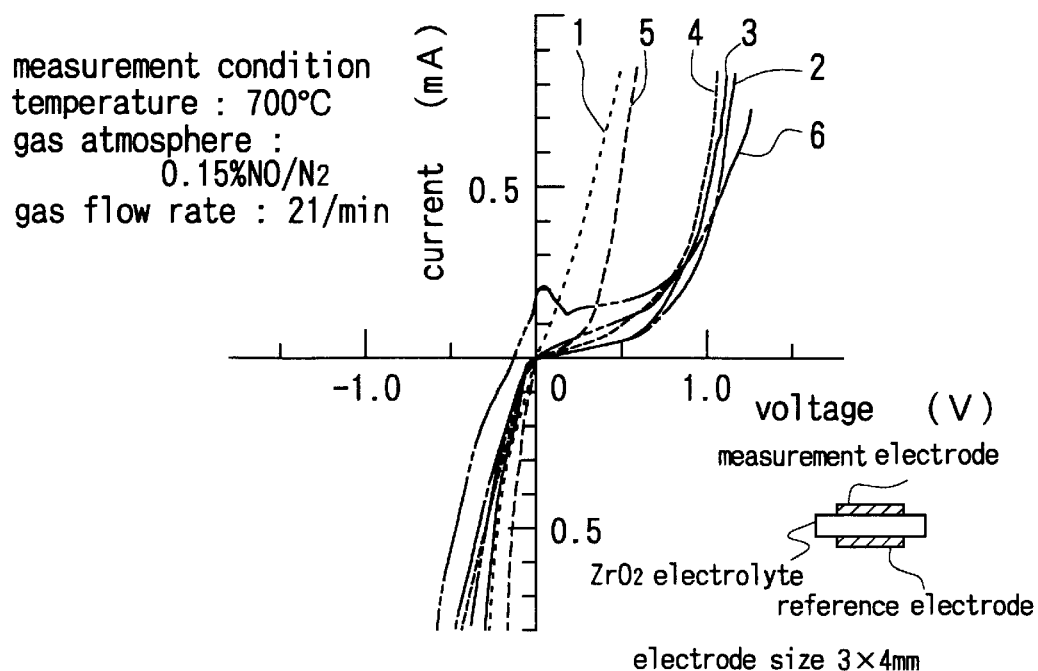
FIG. 6 is a view showing current-voltage characteristics with respect to a NO gas exhibited by electrode examining cells each having, as a cathode, an electrode composed of Pt with addition of Au and various noble metals other than Au.

To the thus obtained electrode examining cells, the measurement gas of which gas composition: 0.15%NO/$N_2$, gas temperature: 700° C., and gas flow rate: 2 L per minute was supplied in order to examine the current-voltage characteristics. The results are shown in FIG. 6. Here, in FIG. 6, the first quadrant shows characteristics of the measurement electrode relative to a $NO_x$ gas, and the third quadrant shows characteristics of the reference electrode relative to a $NO_x$ gas.

From the current-voltage characteristics shown in the first quadrant of FIG. 6, it is apparent that in the case of the sample No.1 (the electrode paste of the Pt-10 wt %$ZrO_2$ composition), the current flowed in proportion to the voltage and the pumping current was large. On the other hand, in the case of the sample No.2 (the electrode paste of the Pt-3 wt % Au-10 wt %$ZrO_2$ composition), the current did not increase abruptly until the applied voltage was in the vicinity of 0.6 V. This result shows that Pt had high NO reducing ability by itself, but by adding Au to Pt, the NO reducing ability was decreased drastically.

The sample No. 3, which was made by further adding Ru to the electrode paste of the sample No. 2, the sample No. 4, which was made by further adding Ir to the electrode paste of the sample No. 2, and the sample No. 6, which was made by further adding Rh to the electrode paste of the sample No. 2, all exhibited the generally identical current-voltage characteristics to the sample No. 2. The reason that the sample No.3 and the sample No. 4 exhibited the characteristics as shown in FIG. 6 is assumed as follows. That is, Ir and Rh added respectively thereto might have been scattered away upon sintering and there was no residuals left in the electrodes. Further, the sample No. 6, which was made by adding Rh exhibited hysteresis, a line that did not pass through the origin. This indicates that, similarly to the Pt-Au electrode (sample No. 2), Au which adhered to the electrode hindered the pumping current from flowing, and Rh which was added thereto caused nitrogen gas accumulated at the electrode to be emitted.

On the contrary, the sample No. 5, which was made by further adding Pd to the electrode paste of the sample No. 2 exhibited the most similar current-voltage characteristics to the sample No. 1. This result shows that the NO reducing ability was lowered due to the addition of Au but recovered by further adding Pd to the Pt-Au electrode.

WORKING EXAMPLE 2

In order to examine an appropriate amount of Pd to be added to a Pt-Au electrode to enhance $NO_x$ gas reducing ability, electrode examining cells were made by further adding Pd in an amount of 0 to 0.5 g to electrode paste of 1 g having a composition of Pt-3 wt % Au-10 wt %$ZrO_2$. The procedures for making the electrode examining cells were the same as the working example 1. Further, the component of the electrode paste used herein is shown in Table 2.

TABLE 2

| Sample No. | Measurement Electrode Component (1 g) | Pd Addition Amount (g) | Reference Electrode |
|---|---|---|---|
| 11 | Pt-10 wt % $ZrO_2$ | — | Pt-10 wt % $ZrO_2$ |
| 12 | Pt-3 wt % Au-10 wt % $ZrO_2$ | — | Pt-10 wt % $ZrO_2$ |
| 13 | Pt-3 wt % Au-10 wt % $ZrO_2$ | 0.05 | Pt-10 wt % $ZrO_2$ |
| 14 | Pt-3 wt % Au-10 wt % $ZrO_2$ | 0.10 | Pt-10 wt % $ZrO_2$ |
| 15 | Pt-3 wt % Au-10 wt % $ZrO_2$ | 0.20 | Pt-10 wt % $ZrO_2$ |
| 16 | Pt-3 wt % Au-10 wt % $ZrO_2$ | 0.50 | Pt-10 wt % $ZrO_2$ |
| 17 | Pd-3 wt % Au-10 wt % $ZrO_2$ | — | Pt-10 wt % $ZrO_2$ |

Figure 7:
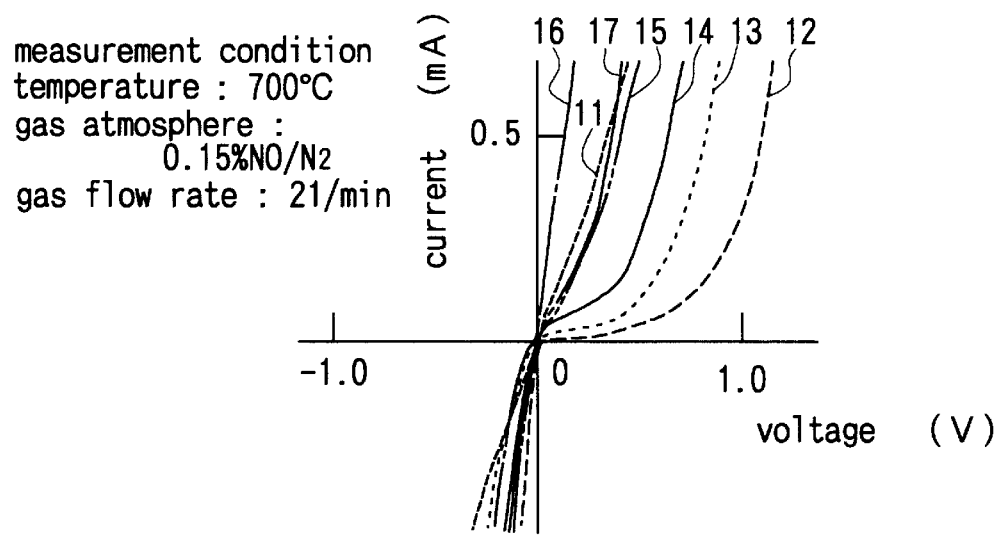
FIG. 7 is a view showing current-voltage characteristics with respect to a NO gas exhibited by electrode examining cells each having, as a cathode, a Pt-Au-Pd electrode with a different addition amount of Pd.

The thus obtained electrode examining cells were examined for the current-voltage characteristics under the same condition as the working example 1. The results are shown in FIG. 7. Here, in FIG. 7, the first quadrant shows characteristics of the measurement electrode relative to a $NO_x$ gas, and the third quadrant shows characteristics of the reference electrode relative to a $NO_x$ gas.

From the current-voltage characteristics shown in the first quadrant of FIG. 7, the following is apparent. That is, in the case of the sample No. 13 made by adding Pd in an amount of 0.05 g to the electrode paste of 1 g having composition of Pt-3 wt % Au-10 wt % $ZrO_2$ (Pd/Au ratio=1.67), the output current was higher than that of the sample No. 12 (composition: Pt-3 wt % Au-10 wt % $ZrO_2$) having no Pd when the same voltage was applied. As the addition amount of Pd increased, the current changed more linearly with the voltage (the characteristics determined by resistance of the zirconia electrolyte), and the voltage required for NO gas reducing decreased, which meant enhancement of NO reducing ability.

Specifically, the sample No. 15, which was made by adding Pd in an amount of 0.2 g (Pd/Au ratio=6.67) exhibited the generally same characteristics as the Pt electrode (the sample No. 11). The sample No. 16, which was made by adding Pd in an amount of 0.5 g (Pd/Au ratio=16.67) exhibited better NO reducing ability than that of the Pt electrode. On the other hand, the sample No. 17 having composition of Pd-3 wt % Au-10 wt % $ZrO_2$ (Pd/Au ratio=29.41) merely exhibited the generally same current-voltage characteristics as the Pt electrode.

WORKING EXAMPLE 3

Assuming that Au which scatters and adheres to the Pt electrode of the $NO_x$ detecting cell 36 lowers $NO_x$ reducing ability, the amount of Au adheres is considered to be 0.1 wt % or less. Here, electrode examining cells were made by further adding Pd in an amount of 0 to 0.2 g to the electrode paste of 1 g having composition of Pt-0.1 wt % Au-10 wt %$ZrO_2$. The procedures for making the electrode examining cell were the same as the working example 1. Further, the component of the electrode paste used herein is shown in Table 3.

TABLE 3

| Sample No. | Measurement Electrode Component (1 g) | Pd Addition Amount (g) | Reference Electrode |
| --- | --- | --- | --- |
| 21 | Pt-10 wt % $ZrO_2$ | — | Pt-10 wt % $ZrO_2$ |
| 22 | Pt-0.1 wt % Au-10 wt % $ZrO_2$ | — | Pt-10 wt % $ZrO_2$ |
| 23 | Pt-0.1 wt % Au-10 wt % $ZrO_2$ | 0.005 | Pt-10 wt % $ZrO_2$ |
| 24 | Pt-0.1 wt % Au-10 wt % $ZrO_2$ | 0.01 | Pt-10 wt % $ZrO_2$ |
| 25 | Pt-0.1 wt % Au-10 wt % $ZrO_2$ | 0.05 | Pt-10 wt % $ZrO_2$ |
| 26 | Pt-0.1 wt % Au-10 wt % $ZrO_2$ | 0.1 | Pt-10 wt % $ZrO_2$ |
| 27 | Pt-0.1 wt % Au-10 wt % $ZrO_2$ | 0.2 | Pt-10 wt % $ZrO_2$ |

Figure 8:
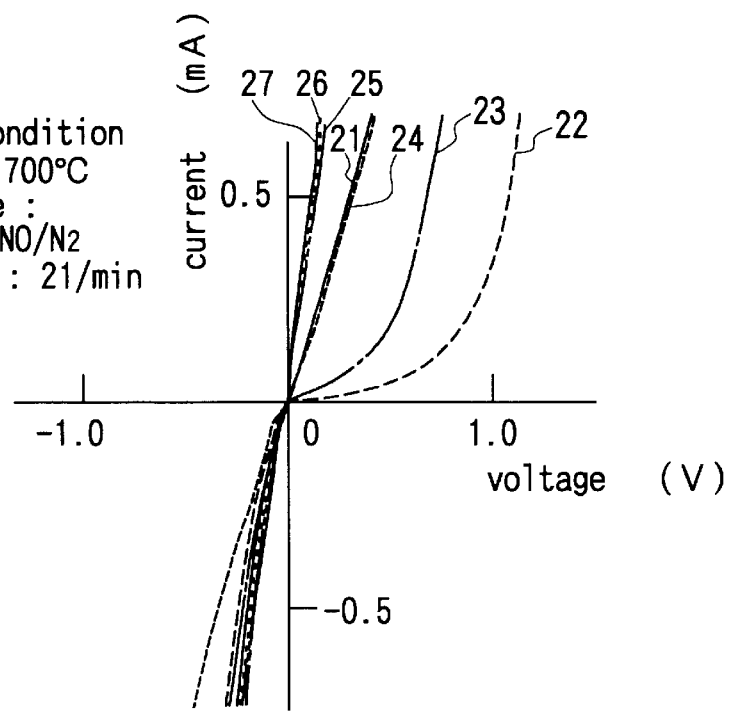
FIG. 8 is a view showing current-voltage characteristics with respect to a NO gas exhibited by electrode examining cells each having, as a cathode, a Pt-Au-Pd electrode with a different addition amount of Pd.

The thus obtained electrode examining cells were examined for the current-voltage characteristics under the same condition as the working example 1. The result are shown in FIG. 8. Here, in FIG. 8, the first quadrant shows characteristics of the measurement electrode relative to a $NO_x$ gas, and the third quadrant shows characteristics of the reference electrode relative to a $NO_x$ gas.

From the current-voltage characteristics shown in the first quadrant of FIG. 8, the following is apparent. That is, in the case of the sample No. 23 made by adding Pd in an amount of 0.005 g to the electrode paste of 1 g having composition of Pt-0.1 wt % Au-10 wt % $ZrO_2$ (Pd/Au ratio=5.0), the output current was higher than that of the same No. 22 having no Pd (composition: Pt-0.1 wt % Au-10 wt % $ZrO_2$). As the addition amount of Pd increased, the current changed more linearly with the voltage (the characteristics determined by resistance of the zirconia electrolyte), and the voltage required for NO gas reducing decreased, which meant enhancement of the $NO_x$ reducing ability.

Specifically, it was found that the sample Nos. 24–27, which were made by adding Pd in an amount of 0.1 g or more (Pd/Au ratio≧10.0) exhibited $NO_x$ reducing ability generally the same as, or better than the Pt electrode (the sample No. 21) despite Au added thereto.

WORKING EXAMPLE 4

In order to examine an appropriate amount of Au to be added to the Pt-Pd electrode of the $NO_x$ detecting cell 36, which causes $NO_x$ reducing ability to be lowered, electrode examining cells were made by further adding Au in an amount of 0 to 0.5 g to electrode paste of 1 g having composition of Pt-50 wt % Pd-10 wt %$ZrO_2$. The procedures for making the electrode examining cells were the same as the working example 1. Further, the component of the electrode paste used herein is shown in Table 4.

TABLE 4

| Sample No. | Measurement Electrode Component (1 g) | Au Addition Amount (g) | Reference Electrode |
| --- | --- | --- | --- |
| 31 | Pt-10 wt % $ZrO_2$ | — | Pt-10 wt % $ZrO_2$ |
| 32 | Pt-50 wt % Au-10 wt % $ZrO_2$ | — | Pt-10 wt % $ZrO_2$ |
| 33 | Pt-50 wt % Au-10 wt % $ZrO_2$ | 0.05 | Pt-10 wt % $ZrO_2$ |
| 34 | Pt-50 wt % Au-10 wt % $ZrO_2$ | 0.10 | Pt-10 wt % $ZrO_2$ |
| 35 | Pt-50 wt % Au-10 wt % $ZrO_2$ | 0.20 | Pt-10 wt % $ZrO_2$ |
| 36 | Pt-50 wt % Au-10 wt % $ZrO_2$ | 0.30 | Pt-10 wt % $ZrO_2$ |
| 37 | Pt-50 wt % Au-10 wt % $ZrO_2$ | 0.50 | Pt-10 wt % $ZrO_2$ |

Figure 9:
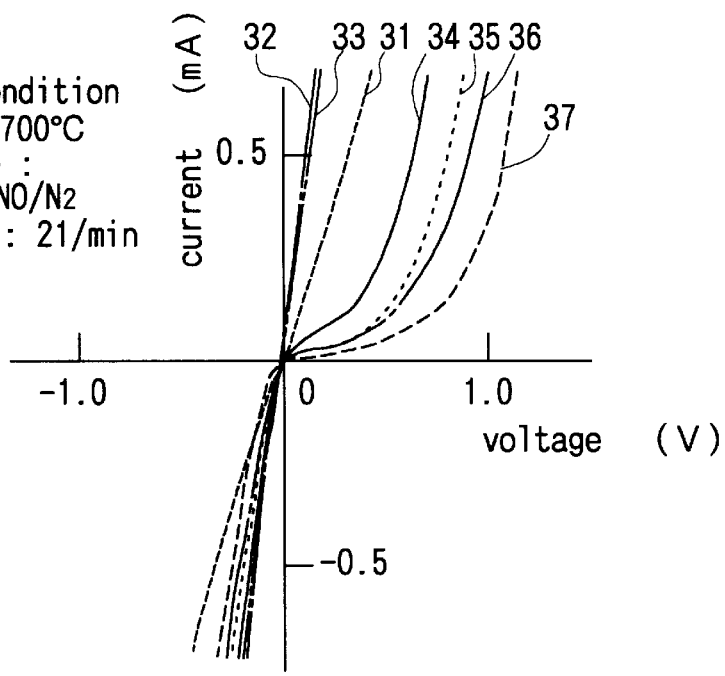
FIG. 9 is a current-voltage characteristics with respect to a NO gas exhibited by electrode examining cells each having, as a cathode, a Pt-Au-Pd electrode with a different addition amount of Au.

The thus obtained electrode examining cells were examined for the current-voltage characteristics under the same condition as the working example 1. The results are shown in FIG. 9. Here, in FIG. 9, the first quadrant shows characteristics of the measurement electrode relative to a $NO_x$ gas, and the third quadrant shows characteristics of the reference electrode relative to a $NO_x$ gas.

From the current-voltage characteristics shown in the first quadrant of FIG. 9, the following is apparent. That is, in the case of the sample No. 37 made by adding Au in an amount of 0.5 g to the electrode paste of 1 g having composition of Pt-50 wt % Pd-10 wt % $ZrO_2$ (Pd/Au ratio=1.0), the voltage required for NO reducing increased drastically. On the other hand, in the case of the sample No. 36 made by adding Au in an amount of 0.3 g (Pd/Au ratio=1.67), the voltage required for NO reducing decreased as compared to the sample No. 37.

As the addition amount of Au decreased, the current changed more linearly with the voltage (the characteristics determined by resistance of the zirconia electrolyte), and the voltage required for $NO_x$ gas reducing decreased, which meant enhancement of $NO_x$ reducing ability. In other words, it was found that the sample No. 34, which was made by adding Au in an amount of 0.1 g (Pd/Au ratio=5.0) exhibited drastic improvement in the $NO_x$ reducing ability, and that the sample Nos. 33 and 32, which were made by adding Au in an amount of 0.05 or less (Pd/Au ratio≧10.0) exhibited better $NO_x$ reducing ability than the Pt electrode (the sample No. 31).

Figure 10:
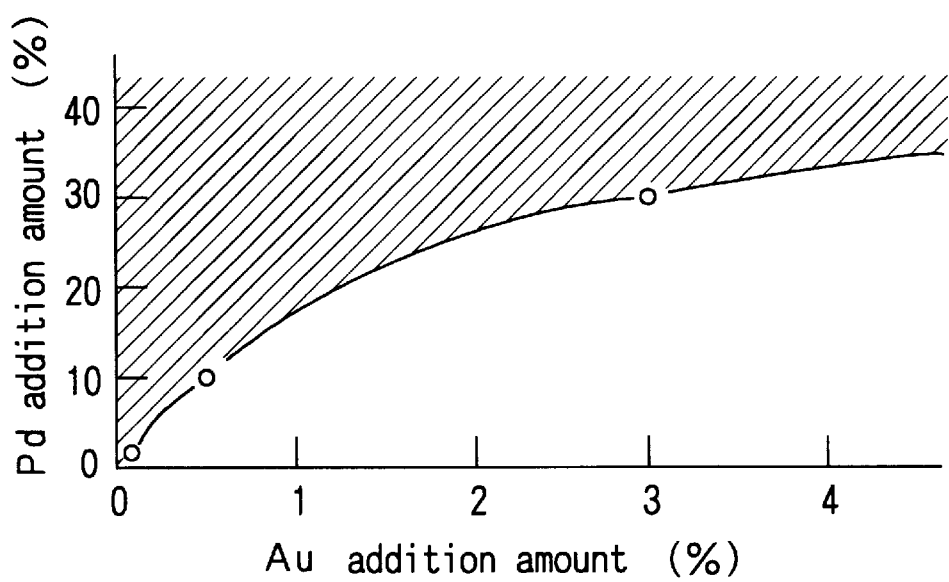
FIG. 10 is a view showing the relation between an addition amount of Pd and an addition amount of Au in order to obtain a Pt-Au-Pd alloy having reducing ability equal to or better than that of Pt.

Based on the findings obtained in the working examples 1–4, consideration was made to find out an appropriate amount of Pd to be added to Au in order to achieve equal or better $NO_x$ reducing ability as compared with the Pt electrode. The results are shown in FIG. 10. As is apparent from the working examples 1–4, equal or better $NO_x$ reducing ability as compared with the Pt electrode was obtained when the addition amount of Pd and the addition amount of Au in the Pt-Au-Pd alloy were kept within the diagonally shaded area shown in FIG. 10.

WORKING EXAMPLE 5

The detecting apparatus 10 shown in FIG. 1 was made in the following procedures. That is, first $ZrO_2$ green sheets each having a 0.5 mm thickness was made in the same procedures as the working example 1. Then, Pt paste having composition of Pt-10 wt % $ZrO_2$ was printed on the front surface and the rear surface of a $ZrO_2$ green sheet by screen printing. In this way, the oxygen gas supplying cell 20 was made. Similarly, Pt paste having composition of Pt-1 wt % Au-10 wt % $ZrO_2$ was printed on the front surface and the rear surface of the $ZrO_2$ green sheets by screen printing. In this way, the oxygen reference electrode generating cell 28 and the oxygen monitoring cell 32 were made.

Next, Pt paste having composition of Pt-1 wt % Au-10 wt % $ZrO_2$ was printed on the front surface of a $ZrO_2$ green sheet by screen printing, thereby constructing the cathode 26b, while Pt paste having composition of Pt-10 wt % $ZrO_2$ was printed on the rear surface thereof thereby constructing the anode 26a. In this way, the oxygen pumping cell 24 was made.

Similarly, Pt paste having composition of Pt-20 wt % Pd-10 wt % $ZrO_2$ was printed on the front surface of a $ZrO_2$ green sheet by screen printing thereby forming the cathode 38b, while Pt paste having composition of Pt-10 wt % $ZrO_2$ was printed on the rear surface thereof thereby forming the anode 38a. In this way, the $NO_x$ detecting cell 36 was made.

Next, in the same procedures except that $Al_2O_3$ powder was used as source powder, an alummina green sheet having a 0.2 mm thickness was made. On the front surface of this alummina green sheet, Pt paste having composition of Pt-10 wt %$ZrO_2$ was printed to construct the heater 40b. In this way, the heater section 40 was made.

Next, each cell and the heater section 40 made above were laminated and bounded together in the following order so as to have a cross section as shown in FIG. 1. That is, the oxygen gas supplying cell 20 was laid over the oxygen reference electrode generating cell 28 and the oxygen monitoring cell 32, which were in turn laid over to the oxygen pumping cell 24, which was in turn laid over the $NO_x$ detecting cell 36, which was in turn laid over the heater section 40. Here, between the oxygen pumping cell 24 and the $NO_x$ detecting cell 36, there were inserted alummina sheets 14a, 14b and 14c each having a thickness of 200 μm in order to insulate the two cells.

The thus obtained layered product was sintered in an electric furnace, whereby the detecting apparatus 10 was obtained. Here, the sintering was conducted in an atmosphere. In addition, the sintering pattern was as follows: ① the temperature was raised up to 450° C. at the temperature raising rate of 50° C. per hour and then the layered product was left at the temperature of 450° C. for an hour in order to degrease the binder added thereto, ② the temperature was raised up to 1,430° C. at the temperature raising rate of 100° C. per hour and the layered product was sintered for one hour, ③ the electric furnace was turned off for slow cooling.

Next, performance tests were conducted on the thus obtained detecting apparatus 10. The performance tests were conducted with an oxygen gas testing apparatus using exhaust gas. This testing apparatus is capable of varying the excess air rate in a gas atmosphere from $\lambda=1.5$ to 0.8 by mixing isobutane and air. The lean ($\lambda=1.2$) gas atmosphere and the rich ($\lambda=0.9$) atmosphere obtained by the testing apparatus were injected a $NO_x$ gas of 0 to 2,000 ppm thereby to produce measurement gases. The measurement gases were supplied to the detecting apparatus 10 thereby to measure output current of the $NO_x$ gas detecting cell 36. Here, a NO gas was injected to the measurement gases using an injector at an interval of 50 ppm or 100 ppm such that the $NO_x$ gas concentration was between a range of 0 and 200 ppm.

The operation conditions of the detecting apparatus 10 was as follows.

Heating temperature of heater: 700° C.,

Current of oxygen gas supplying cell: 1 mA

Applied voltage to oxygen gas reference electrode generating cell: 0.5 V

Applied voltage to oxygen pumping cell: 0.3 V

Applied voltage to $NO_x$ detecting cell: 0.6 V

Excess air rate of exhaust gas: $\lambda=1.2$, 0.9

Temperature of exhaust gas: 450° C.

Shown in FIG. 11 is the output current of the $NO_x$ detecting cell 36 when the NO gas concentration changed in the gas atmosphere with the excess air rate of $\lambda=0.9$, 1.2. As is apparent from FIG. 11, the detecting apparatus 10 consistent with this preferred embodiment generated output current in proportion to the NO gas concentration irrespective of the change in the atmosphere between lean and rich. This is because the atmosphere in the gas introducing chamber 16 was maintained under a lean state by the oxygen gas supplying cell 20. In addition, it is also because a Pt-Pd electrode was used as the cathode 38b of the $NO_x$ detecting cell 36, whereby decrease in activity relative to $NO_x$ due to Au adhesion was suppressed.

WORKING EXAMPLE 6

The detecting apparatus 10 made in the working example 5 was examined for its responsivity to a $NO_x$ gas. As a comparative example, a detecting apparatus was made using a conventionally-used electrode having composition of Pt-40 wt % Rh-10 wt % $ZrO_2$ as a cathode of a $NO_x$ detecting cell to examine its responsivity to a $NO_x$ gas. Here, to examine the responsivity, first, a NO gas was injected into a gas atmosphere of an excess air rate of $\lambda=1.2$ to produce a measurement gas, the measurement gas was supplied to the $NO_x$ detecting cell, and then the $NO_x$ gas concentration was abruptly changed from 500 ppm to 1,000 ppm. Here, change in the output current of the $NO_x$ detecting cell generated at this time was examined to evaluate the responsivity. The results are shown in FIG. 12.

In the case of the detecting apparatus comprising the $NO_x$ detecting cell using the Pt-Rh electrode as the cathode, upon abruptly changing the $NO_x$ gas concentration rate to 1,000 ppm, the output current exceeded 10 μA and dropped to about 8 μA a few minutes after. Thereafter, the output current gradually decreased as time went by. These findings show that in the case of the Pt-Rh electrode, influence of the adsorbed oxygen was large, and therefore, it was difficult to detect abrupt change in the NO concentration faithfully. On the contrary, in the case of detecting apparatus comprising the NO detecting cell using the Pt-Pd electrode as the cathode, the output current responded immediately to the change in the NO gas concentration. This indicates the capability of detecting the change in the $NO_x$ gas concentration faithfully.

WORKING EXAMPLE 7

Figure 13:
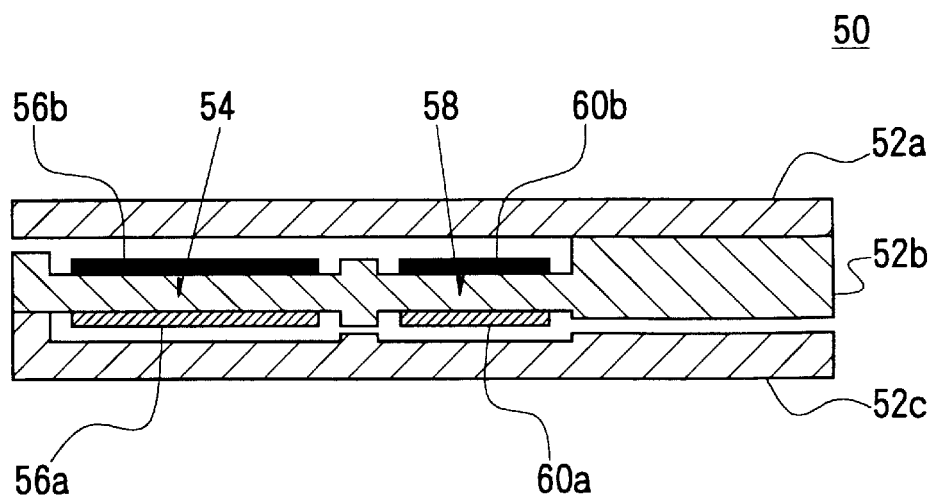
FIG. 13 is a cross sectional view showing a $NO_x$ gas detecting apparatus used in the experiments.

In order to determine an optimum addition amount of Rh of a Pt-Pd-Rh electrode, detecting apparatuses were made using Pt-Pd-Rh electrodes with different Rh addition amounts as the cathodes, and the detecting apparatuses were examined for their current-voltage characteristics. Shown in FIG. 13 is a cross section of the detecting apparatus 50 used in the experiment.

First, $ZrO_2$ green sheets each having a thickness of 0.5 mm were made in the same procedures as the working example 1. Next, as shown in FIG. 13, an anode 56a and a cathode 56b constructing a pumping cell 54 were printed on a green sheet 52b by screen printing, and so were an anode 60a and a cathode 60b constituting a detecting cell 58. Next, green sheets each having a pre-determined shape were laminated over each side of the green sheet 52b thereby forming a predetermined projections and depressions on the surface of the green sheet 52b. Further, green sheets 52a and 52c were laminated over each side of the green sheet 52b. Thereafter, by sintering the layered product in an atmosphere, the detecting apparatus 50 was obtained.

Here, the sintering condition was as follows. First, the temperature was raised at the temperature raising rate of 50° C. per hour to keep the layered product was at the temperature of 450° C. for one hour, then the temperature was raised at the temperature raising rate of 100° C. per hour to keep the layered product at 1,430° C. for one hour, and finally the layered product was slowly cooled in an atmosphere. The composition of the paste used to form electrodes of each cell is shown in Table 5. Here, it should be noted that in this preferred embodiment and the working examples 8–10, Au is adhered to the cathode 60b of the detecting cell through the sintering process described above.

TABLE 5

| Sample | Pumping Cell | | Detecting Cell | | | |
|---|---|---|---|---|---|---|
| No. | Cathode | Anode | Cathode | | | Anode |
| 41 | Pt-3% Au-10% $ZrO_2$ | Pt-10% $ZrO_2$ | Pt-10% $ZrO_2$ (1 g) | Pd (0.3 g) | | Pt-10% $ZrO_2$ |
| 42 | Pt-3% Au-10% $ZrO_2$ | Pt-10% $ZrO_2$ | Pt-10% $ZrO_2$ (1 g) | Pd (0.3 g) | Rh (0.05 g) | Pt-10% $ZrO_2$ |
| 43 | Pt-3% Au-10% $ZrO_2$ | Pt-10% $ZrO_2$ | Pt-10% $ZrO_2$ (1 g) | Pd (0.3 g) | Rh (0.1 g) | Pt-10% $ZrO_2$ |
| 44 | Pt-3% Au-10% $ZrO_2$ | Pt-10% $ZrO_2$ | Pt-10% $ZrO_2$ (1 g) | Pd (0.3 g) | Rh (0.2 g) | Pt-10% $ZrO_2$ |
| 45 | Pt-3% Au-10% $ZrO_2$ | Pt-10% $ZrO_2$ | Pt-10% $ZrO_2$ (1 g) | Pd (0.3 g) | Rh (0.3 g) | Pt-10% $ZrO_2$ |
| 46 | Pt-3% Au-10% $ZrO_2$ | Pt-10% $ZrO_2$ | Pt-10% $ZrO_2$ (1 g) | Pd (0.3 g) | Rh (0.4 g) | Pt-10% $ZrO_2$ |
| 47 | Pt-3% Au-10% $ZrO_2$ | Pt-10% $ZrO_2$ | Pt-10% $ZrO_2$ (1 g) | Pd (0.3 g) | Rh (0.6 g) | Pt-10% $ZrO_2$ |

Next, current-voltage characteristics of each of the thus obtained detecting apparatuses were measured. The measurement was performed under the condition where the gas temperature: 700° C., the gas atmosphere: 0.1%NO/$N_2$, and the gas flow rate: 2 L per minute. In the measurement, the current-voltage characteristics were measured three times consecutively while changing the voltage applied to the detecting cell from 0 V to 1.2 V at the voltage application rate of 10 mV per second.

Figure 14:
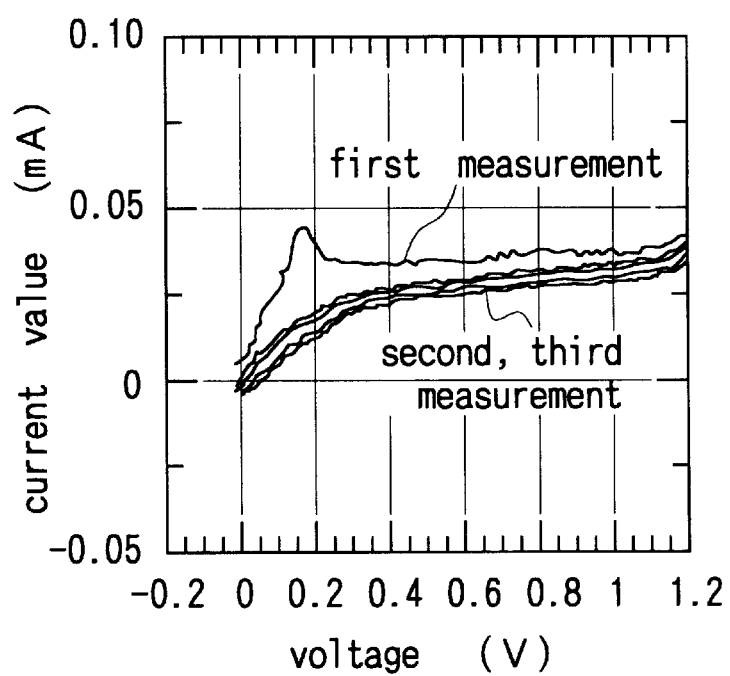
FIG. 14 is a view showing current-voltage characteristics exhibited by a detecting cell having, as a cathode, an electrode composed of Pt-10 wt % $ZrO_2$ (1 g)+Pd (0.3 g)+Rh (0.3 g) (Sample No. 45)

In FIG. 14, the measurement results of the sample No. 45 (the Rh addition amount of 20 wt %) are shown. As is apparent from FIG. 14, in the case where Rh was further added to the Pt-Pd electrode, a peak was observed in the current value in the first measurement. This peak was caused because the two current values were added together: one derived from oxygen generated upon the NO decomposition and the other derived from oxygen that had been adhered to the electrode and ejected therefrom. However, no peak was observed in either second or third measurement and rather there was exhibited limiting current characteristic corresponding to the oxygen concentration derived by the NO gas decomposition. These findings show that the Pt-Pd-Rh electrode was a little inferior in terms of the startability, yet capable of measuring the NO gas concentration accurately provided that it was used consecutively. Although not illustrated, the other sample Nos. 42–44, 46 and 47 to which Rh was added exhibited the similar results. That is, no peak caused by ejection of adsorbed oxygen was observed in the second measurement and after.

Figure 15:
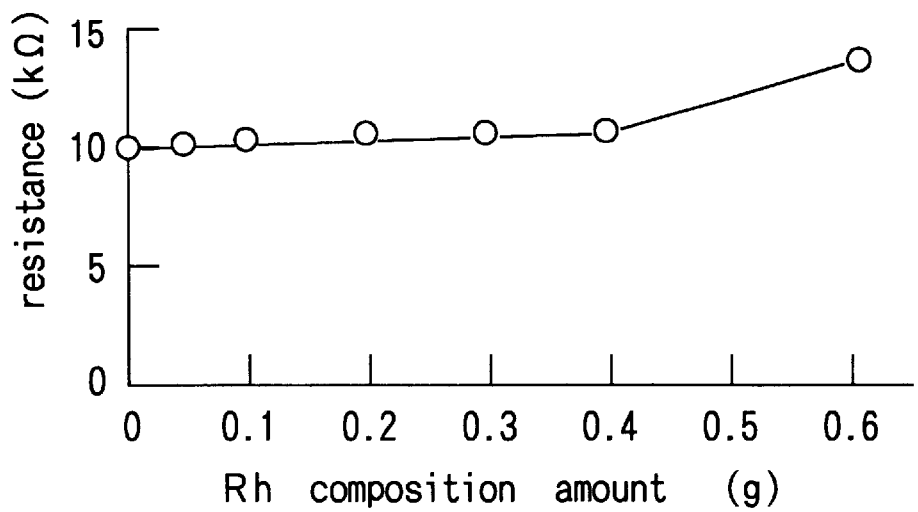
FIG. 15 is a view showing the relation between a compound amount of Rh and resistance of a detecting cell.

Next, based on the measurement results showing the current-voltage characteristics of the sample Nos. 41–47, the resistance was calculated from the current at the voltage of 0 V to 0.1 V to examine the relation between the composition amount of Rh and the resistance of the detecting cell. The results are shown in FIG. 15. Up to the Rh composition amount of 0.4 g relative to Pt-10 wt %$ZrO_2$ (1 g)-Pd(0.3 g) (the sample Nos. 41–46, the Rh addition amount of 0 to 25 wt %), the resistance remained generally constant. However, when the Rh composition amount was 0.6 g, the resistance increased rapidly. The angle of the rising edge in the current-voltage characteristics, as shown in FIG. 14, largely depends on the resistance of the detecting cell. The larger the resistance is, the smaller the angle of the rising edge will be. That is, increase in the resistance of the detecting cell results in increase in the limiting current generating voltage. Accordingly, it is preferred that an upper limit be provided on the Rh composition amount such that an intended limiting current voltage is obtained.

Figure 16:
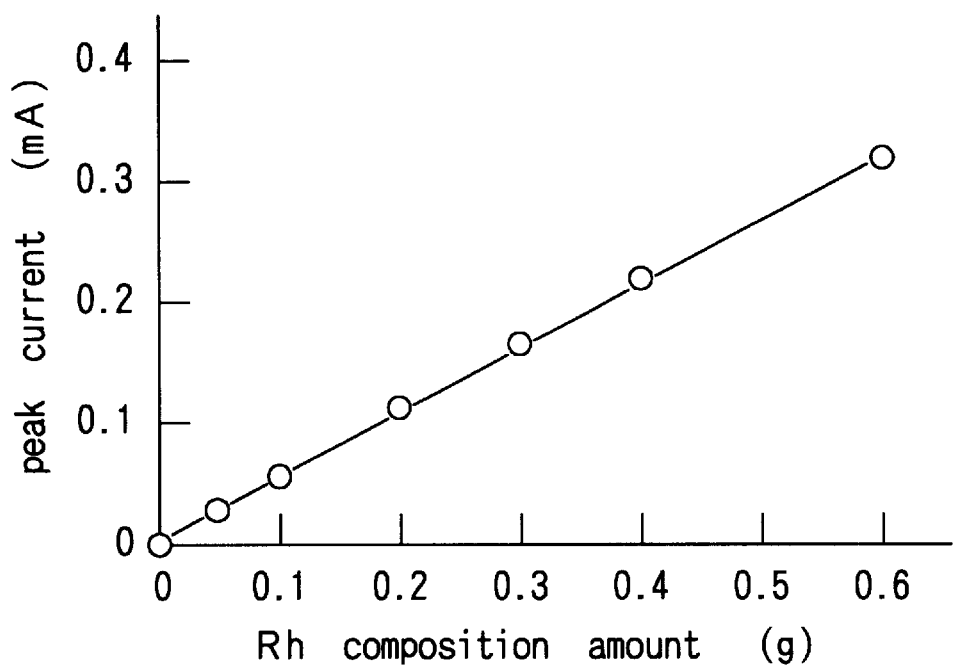
FIG. 16 is a view showing the relation between a compound amount of Rh and a peak current.

Shown in FIG. 16 is the relation between the peak current which was detected in the first measurement of the current-voltage characteristics and the Rh composition amount. As is apparent from FIG. 16, the peak voltage increased in proportion to the increase in the Rh composition amount. This is because a larger amount of oxygen adheres to the electrode as the Rh composition amount increases. Increase in the peak voltage results in decrease in the startability. Accordingly, it is preferred that an upper limit be provided on the Rh composition amount such that an intended startability is obtained.

WORKING EXAMPLE 8

In accordance with the same procedures as the working example 7, seven different types of detecting apparatuses (the sample Nos. 41–47) were made with different addition amounts of Rh to examine influence on current-voltage characteristics exerted by heat treatment. The heat treatment was conducted by heating each of the manufactured detecting apparatuses to 900° C. in an atmosphere and by applying voltage of 1 V for ten minutes.

Figure 17:
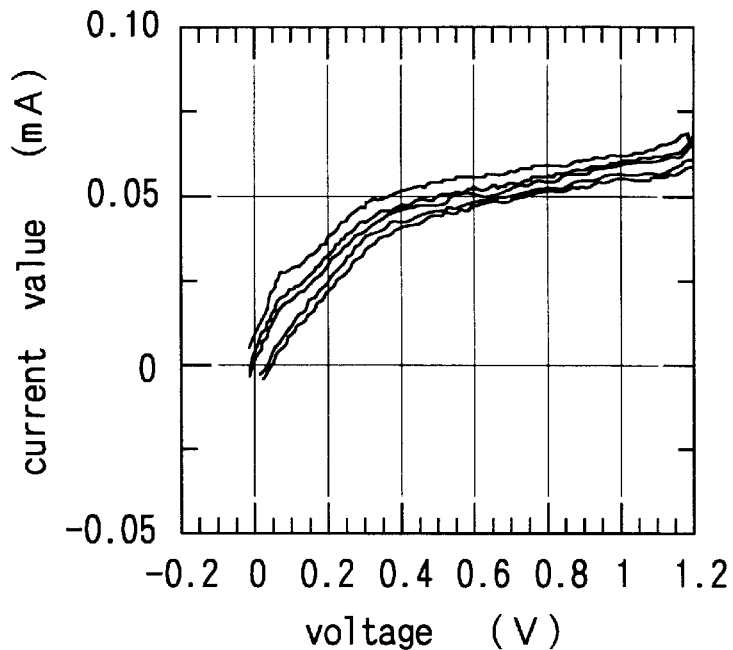
FIG. 17 is a view showing current-voltage characteristics exhibited before conducting the heat treatment by the detecting cell having, as a cathode, an electrode composed of Pt-10 wt % $ZrO_2$ (1 g)+Pd (0.3 g)+Rh (0.3 g) (Sample No. 45)
Figure 18:
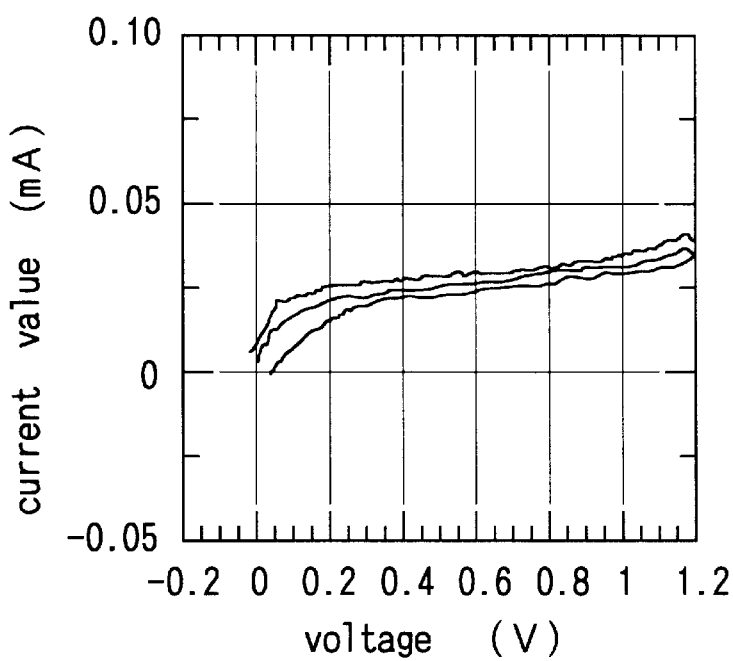
FIG. 18 is a view showing current-voltage characteristics exhibited after conducting the heat treatment by the detecting cell having, as a cathode, an electrode composed of Pt-10 wt % $ZrO_2$ (1 g)+Pd (0.3 g)+Rh (0.3 g) (Sample No. 45)

Next, each sample before the heat treatment and after the heat treatment was subjected to the following operation and the operation was repeated three times. That is, first voltage was applied to the sample while varying the voltage from 0 V to 1.2 V at the voltage application rate of 10 mV per second under the condition where the gas temperature: 700° C., the gas atmosphere: 0.2%NO/$N_2$, the gas flow rate: 2 L per minute, whereby the oxygen adhered to the electrode was caused to be ejected. Thereafter, the current-voltage characteristics were measured under the same condition. FIGS. 17 and 18 respectively show the current-voltage characteristics of the detecting apparatus of the sample No. 45 measured before and after the heat treatment.

Before the heat treatment, the sample No. 45 exhibited the limiting current generating voltage of about 0.3 V and the current value in the limiting current region was about 0.05 mA. On the other hand, after the heat treatment, the limiting current voltage was about 0.2 V and the current value in the limiting current region was about 0.025 mA, which meant that the limiting current region was expanded and the current was lowered. In addition, even if the same heat treatment was conducted again on the sample which had been heat treated already, the change in the output current was small.

Figure 19:
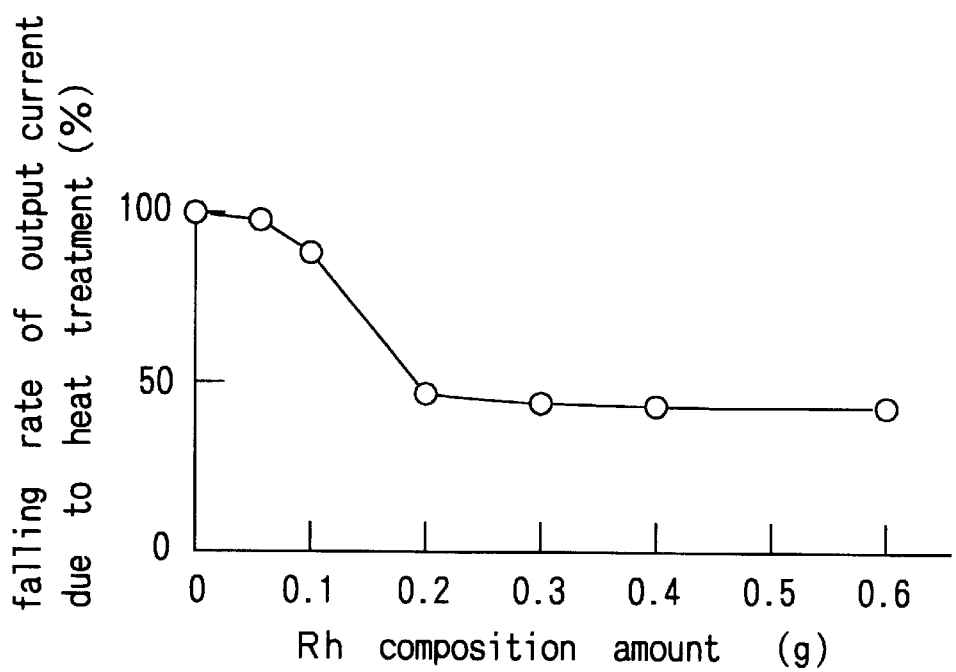
FIG. 19 is a view showing the relation between a composition amount of Rh in a Pt-Pd-Rh electrode and a falling rate of output current due to the heat treatment.

FIG. 19 shows the relation between the Rh composition amount and the falling rate of the output current. Here, the "falling rate of the output current" refers to the value obtained by the expression (output current after heat treatment/output current before heat treatment)×100. From FIG. 19, it is apparent that the output current fell as the Rh composition amount increased. In addition, when the Rh composition amount is 0.2 g or more (the Rh addition amount of 14.3 wt %), the output current fell more than 50%, whereby the falling rate of the output current became saturated so that further increase in the Rh composition amount did not cause any further drop in the output current.

Figure 20:
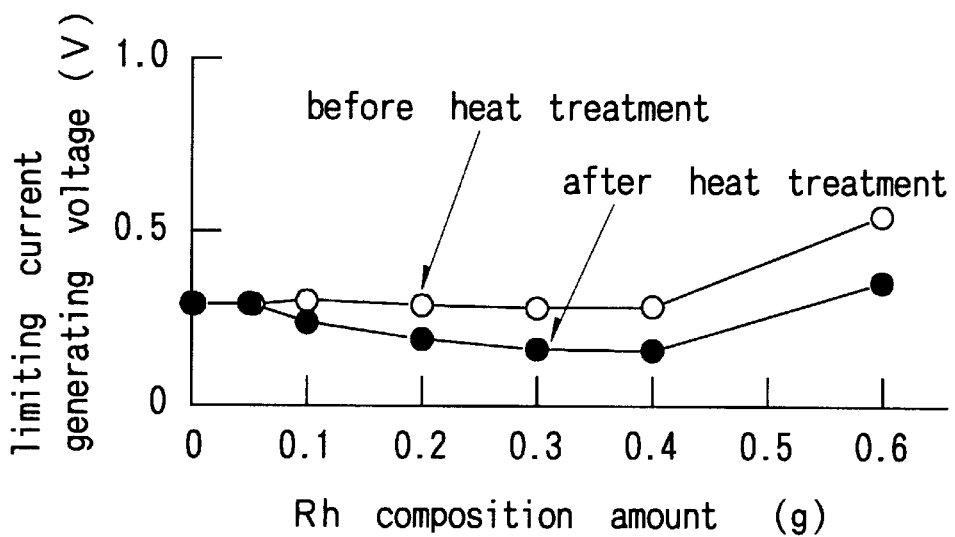
FIG. 20 is a view showing relation between a composition amount of Rh in the Pt-Pd-Rh electrode and a limiting current generating voltage after the heat treatment.

FIG. 20 shows the relations of the Rh composition amount with the limiting current generating voltage before and after the heat treatment respectively. In the case of the samples before the heat treatment, when the Rh composition amount was less than 0.4 g (the Rh addition amount of 25 wt %), the limiting current generating voltage slightly fell as the Rh composition amount increased. However, when the Rh composition amount was 0.6 g, the limiting current generating voltage exceeded 0.3 V. On the other hand, after conducting the heat treatment on the sample containing Rh added thereto, the limiting current generating voltage fell as compared with that of before the heat treatment. Moreover, the falling rate the limiting current generating voltage was apt to increase as the Rh composition amount increased. Especially, when the Rh composition amount was 0.2 g to 0.4 g (the Rh addition amount of 14.3 to 25 wt %), the limiting current generating voltage dropped to about 0.2 V and the limiting current region expanded.

The above findings indicate that by conducting heating treatment in which the Pt-Pd-Rh electrode was heated in an atmosphere while applying voltage, the limiting current generating voltage shifts toward a lower voltage. This is because by conducting heating treatment on the Pt-Pd-Rh electrode, there is formed a thin oxide film having $Rh_2O_3$ as a main component on the surface of the electrode. This oxide film is considered to control the diffusion rate of oxygen in the detecting cell.

WORKING EXAMPLE 9

Detecting apparatus 10 having the configuration as shown in FIG. 1 was made in the same procedures as the working example 5 except that the cathode 38b of the $NO_x$ detecting cell 36 was constructed of Pt paste having composition of Pt-10%$ZrO_2$ (1 g)+Pd (0.3 g) and Rh (0.3 g) combined thereto. Then, performance tests of the thus obtained detecting apparatus 10 were carried out. Here, the operation conditions of the detecting apparatus 10 were the same as that of the working example 5 except that the voltage applied to the $NO_x$ detecting cell was 0.4 V.

Figure 21:
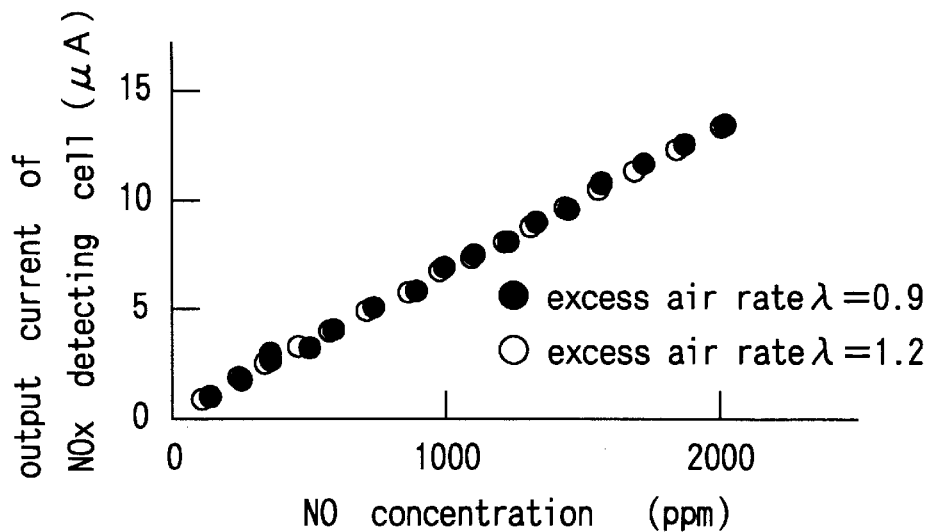
FIG. 21 is a view showing relation between an output current of a $NO_x$ detecting apparatus having a Pt-Pd-Rh electrode as a cathode and a NO gas concentration.

Shown in FIG. 21 is the output current of the $NO_x$ detecting cell 36 when the NO gas concentration was changed in the gas atmosphere with the excess air rate of λ=0.9, 1.2. As is apparent from FIG. 21, the detecting apparatus 10 consistent with this preferred embodiment generated output current in proportion to the NO gas concentration irrespective of change in the atmosphere between lean and rich. This is because the atmosphere in the gas introducing chamber 16 was maintained under a lean state by the oxygen gas supplying cell 20. In addition, this is also because a Pt-Pd-Rh electrode was used as the cathode 38b of the $NO_x$ detecting cell 36, whereby the limiting current generating voltage shifted toward a lower voltage. As the result, although the voltage applied to the $NO_x$ detecting cell 36 was lowered, output current was obtained in correspondence to the $NO_x$ concentration.

WORKING EXAMPLE 10

Figure 22:
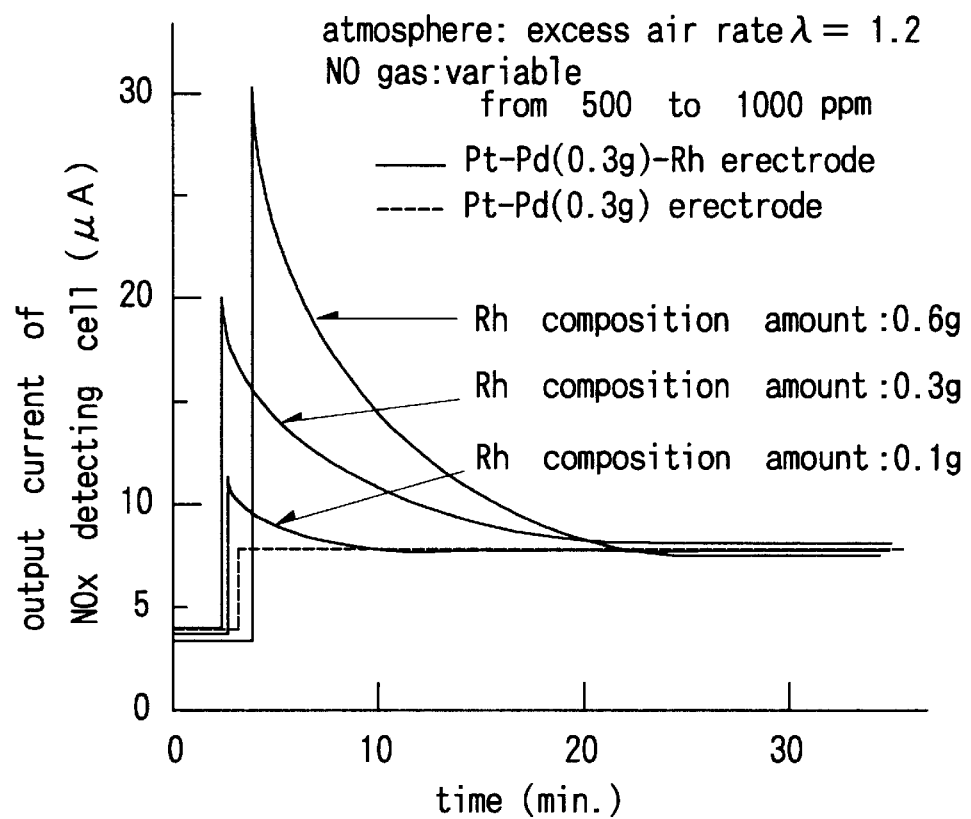
FIG. 22 is a view showing responsivity of a $NO_x$ detecting apparatus having a Pt-Pd electrode or a Pt-Pd-Rh electrode as a cathode of the $NO_x$ detecting cell.

The detecting apparatuses 10 having the configuration as shown in FIG. 1 were made in the same procedures as the working example 5 except that the cathode 38b of the $NO_x$ detecting cell 36 was constructed of Pt paste having composition of Pt-10%$ZrO_2$ (1 g)+Pd (0.3 g) and Rh combined in different amounts thereto. Here, in this preferred embodiment, there were four different Rh composition amounts: 1 g, 0.1 g, 0.3 g and 0.6 g (0 wt %, 7.7 wt %, 20 wt %, and 33.3 wt % respectively in terms of the Rh addition amount). Then, the thus obtained detecting apparatuses 10 were examined for the responsivity. The results are shown in FIG. 22.

In the case where a Pt-Pd electrode was used as the cathode 38b of the $NO_x$ detecting cell 36, the output current responded to change in the $NO_x$ gas concentration immediately, and thus detection of $NO_x$ was carried out accurately. On the other hand, in the case where a Pt-Pd-Rh electrode was used as the cathode 38b of the $NO_x$ detecting cell 36, the output current exceeded 10 μA in response to abrupt change in the $NO_x$ gas concentration to 1,000 ppm, and thereafter gradually decreased as the time went by. In addition, the larger the Rh composition amount was, the larger the change in the output current was in response to the abrupt change in the $NO_x$ gas concentration and the longer it took before the output current stabilized. This is because the difference in the Rh composition amount resulted in the change in the ejection time of the oxygen gas adhered to the electrode.

The foregoing findings show that the larger the Rh composition amount in the Pt-Pd-Rh electrode was, the less the responsivity to the $NO_x$ would be. Accordingly, in order to obtain an intended responsivity, the Rh composition amount needs to be set to an optimum value.

The foregoing description have been given to the preferred embodiments of the present invention in detail. However, the present invention is not limited to the above preferred embodiments and various modifications are possible without departing from the spirit and the scope of the present invention.

For example, in the above preferred embodiments, the detecting apparatus 10 comprises an oxygen gas supplying cell 20. Yet, the oxygen supplying cell 20 may be omitted in the case where the measurement gas is always maintained in a lean state. Also, in the above preferred embodiment, the residual oxygen concentration is measured with the use of the oxygen reference electrode generating cell 28. Instead, a gas of which oxygen concentration is known (for example atmosphere) may be introduced into one of the cells in the detecting apparatus 10 so that it functions as a reference electrode upon measuring the residual oxygen concentration.

Further, in the above preferred embodiment, description has been given mainly to a so-called "current-type" $NO_x$ detecting apparatus, which causes $NO_x$ contained in a measurement gas to be decomposed and measures the current generated upon the decomposition to determine the $NO_x$ gas concentration. Yet, electrode materials having Pt-Pd composition consistent with the present invention are equally applicable also to a so-called "electromotive force type" $NO_x$ gas detecting apparatus to achieve the equal effect. This type of apparatus measures an electromotive force generated between a measurement electrode to which a measurement gas is introduced and a reference electrode so as to determine the $NO_x$ gas concentration.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A $NO_x$ gas detecting apparatus comprising:

an oxygen pumping cell for removing oxygen from a measurement gas; and a $NO_x$ detecting cell positioned downstream from said oxygen pumping cell to detect concentration of $NO_x$ in said measurement gas, said $NO_x$ detecting cell being configured to measure current which flows when oxygen generated from reducing $NO_x$ is pumped, wherein said $NO_x$ detecting cell has a $NO_x$ detecting cell cathode made of an electrode material and the electrode material comprises a Pt-Au-Pd alloy which includes Pd and Au in a Pd to Au weight ratio of not less than 1.67.

2. The $NO_x$ gas detecting apparatus according to claim 1, wherein the electrode material includes Pd in an amount of from 1 to 90 wt % with respect to Pt.

3. A $NO_x$ gas detecting apparatus comprising:

an oxygen pumping cell for removing oxygen from a measurement gas and including an oxygen pumping cell cathode; and a $NO_x$ detecting cell positioned downstream from said oxygen pumping cell to detect concentration of $NO_x$ in said measurement gas, said $NO_x$ detecting cell being configured to measure current which flows when oxygen generated from reducing $NO_x$ is pumped, wherein said $NO_x$ detecting cell includes a $NO_x$ detecting cell cathode and an $NO_x$ detecting cell anode formed on a solid electrolyte having oxygen ion conductivity, the former being disposed on a measurement gas introducing side and the latter being disposed on the other side, and the $NO_x$ detecting cell cathode is made of an electrode material and the electrode material comprises a Pt-Au-Pd alloy which includes Pd and Au in a Pd to Au weight ratio of not less than 1.67.

4. The $NO_x$ gas detecting apparatus according to claim 3, wherein said solid electrolyte comprises an electrolyte selected from the group consisting of a zirconia-base solid electrolyte, a ceria-base solid electrolyte, and a bismuth oxide-base solid electrolyte.

5. The $NO_x$ gas detecting apparatus according to claim 3, wherein the electrode material includes Pd in an amount of from 1 to 90 wt % with respect to Pt.

6. The $NO_x$ gas detecting apparatus according to claim 3, wherein the oxygen pumping cell cathode comprises a cermet material including a Pt-Au alloy.

7. A $NO_x$ gas detecting apparatus comprising:

an oxygen pumping cell for removing oxygen from a measurement gas;

an oxygen monitoring cell for measuring an amount of residual oxygen contained in the measurement gas from which oxygen has been removed by said oxygen pumping cell; and a $NO_x$ detecting cell positioned downstream from said oxygen pumping cell to detect concentration of $NO_x$ in said measurement gas, said $NO_x$ detecting cell being configured to measure current which flows when oxygen generated by reducing $NO_x$ in the measurement gas is pumped, said current being corrected based on the amount of residual oxygen measured by said oxygen monitoring cell, wherein:

said oxygen pumping cell includes a cathode made of a cermet material including a Pt-Au alloy;

said $NO_x$ detecting cell includes a $NO_x$ detecting cell cathode made of a cermet material; and said electrode material comprises a Pt-Au-Pd alloy which includes Pd and Au in a Pd to Au weight ratio of not less than 1.67.

8. The $NO_x$ gas detecting apparatus according to claim 7, wherein the at least one alloy includes Pd in an amount of from 1 to 90 wt % with respect to Pt.

* * * * *